United States Patent
Rehberger et al.

(10) Patent No.: US 11,298,383 B2
(45) Date of Patent: Apr. 12, 2022

(54) LACTOBACILLUS AND BACILLUS BASED DIRECT FED MICROBIAL TREATMENT FOR POULTRY AND METHOD OF USE

(71) Applicant: Church & Dwight Co., Inc., Ewing, NJ (US)

(72) Inventors: Thomas Rehberger, Wauwatosa, WI (US); Evan Hutchison, Milwaukee, WI (US); Alexandra Smith, Greendale, WI (US)

(73) Assignee: Church & Dwight Co., Inc., Princeton, NJ (US)

( * ) Notice: Subject to any disclaimer, the term of this patent is extended or adjusted under 35 U.S.C. 154(b) by 167 days.

(21) Appl. No.: 15/601,656

(22) Filed: May 22, 2017

(65) Prior Publication Data

US 2017/0333496 A1    Nov. 23, 2017

Related U.S. Application Data

(60) Provisional application No. 62/339,615, filed on May 20, 2016.

(51) Int. Cl.
| | |
|---|---|
| *A23K 10/18* | (2016.01) |
| *A23K 20/10* | (2016.01) |
| *A23K 50/75* | (2016.01) |
| *A61K 9/19* | (2006.01) |
| *A61K 35/742* | (2015.01) |
| *A61K 35/747* | (2015.01) |
| *A61K 9/00* | (2006.01) |

(52) U.S. Cl.
CPC ............ *A61K 35/747* (2013.01); *A23K 10/18* (2016.05); *A23K 20/10* (2016.05); *A23K 50/75* (2016.05); *A61K 9/0053* (2013.01); *A61K 9/19* (2013.01); *A61K 35/742* (2013.01); *A23Y 2220/67* (2013.01); *A23Y 2220/79* (2013.01)

(58) Field of Classification Search
None
See application file for complete search history.

(56) References Cited

U.S. PATENT DOCUMENTS

| | | | |
|---|---|---|---|
| 6,051,219 A | 4/2000 | Kubota | |
| 6,140,106 A | 10/2000 | Lawler et al. | |
| 6,162,634 A | 12/2000 | Lawler et al. | |
| 6,162,635 A | 12/2000 | Lawler et al. | |
| 6,422,174 B1 | 7/2002 | Horikawa et al. | |
| 6,660,294 B2 | 12/2003 | Maruta et al. | |
| 6,812,022 B1 | 11/2004 | Aonuma | |
| 6,989,370 B2 | 1/2006 | Fahrlander et al. | |
| 7,247,299 B2 | 7/2007 | Lin et al. | |
| 7,618,640 B2 | 11/2009 | Rehberger et al. | |
| 7,754,469 B2 | 7/2010 | Baltzley et al. | |
| 8,021,654 B2 | 9/2011 | Rehberger et al. | |
| 8,420,138 B2 | 4/2013 | Knap et al. | |
| 8,455,238 B2 | 6/2013 | Baltzley et al. | |
| 8,506,951 B2 | 8/2013 | Rehberger et al. | |
| 8,540,981 B1 | 9/2013 | Wehnes et al. | |
| 8,642,317 B2 | 2/2014 | Zhou et al. | |
| 8,722,058 B2 | 5/2014 | Rehberger et al. | |
| 8,741,280 B2 | 6/2014 | Cantor et al. | |
| 8,802,079 B2 | 8/2014 | Knap et al. | |
| 9,005,601 B2 | 4/2015 | Hargis et al. | |
| 9,011,836 B2 | 4/2015 | Rehberger et al. | |
| 9,089,151 B2 | 7/2015 | Davis et al. | |
| 9,144,588 B2 | 9/2015 | Ruhbio et al. | |
| 9,247,757 B2 | 2/2016 | Schmidt et al. | |
| 2013/0330308 A1* | 12/2013 | Millan | A61K 35/747 424/93.41 |
| 2014/0037582 A1 | 2/2014 | Romero et al. | |
| 2015/0079058 A1 | 3/2015 | Nielsen et al. | |
| 2015/0118203 A1 | 4/2015 | Boyette et al. | |
| 2015/0216915 A1 | 8/2015 | Frouel et al. | |
| 2015/0230498 A1 | 8/2015 | Davis et al. | |
| 2015/0250831 A1 | 9/2015 | Rehberger et al. | |
| 2015/0257400 A1 | 9/2015 | Reuter et al. | |
| 2015/0290254 A1 | 10/2015 | Remus et al. | |
| 2015/0306154 A1 | 10/2015 | Davis et al. | |
| 2016/0007614 A1 | 1/2016 | Rubio et al. | |
| 2016/0120919 A1 | 5/2016 | Ashida et al. | |
| 2017/0014516 A1* | 1/2017 | Petersen | A61K 47/26 |

FOREIGN PATENT DOCUMENTS

| | | |
|---|---|---|
| WO | 2015160960 A1 | 10/2015 |
| WO | 2015175667 A1 | 11/2015 |
| WO | 2016022779 A1 | 2/2016 |
| WO | 2016030441 A1 | 3/2016 |
| WO | 2016060934 A1 | 4/2016 |

(Continued)

OTHER PUBLICATIONS

Fascella et al., Acta Horticulturae, No. 1099, pp. 291-295 (2015).*

(Continued)

*Primary Examiner* — Soren Harward
*Assistant Examiner* — Paul D Pyla
(74) *Attorney, Agent, or Firm* — Church & Dwight Co., Inc.

(57) ABSTRACT

This disclosure relates generally to a microbial treatment for poultry. More particularly, the disclosure relates to a direct fed microbial composition including one or more lactic acid bacteria strains in combination with one or more *Bacillus* bacteria strains configured to inhibit gastrointestinal pathogens in a bird. A method of use is also disclosed herein.

6 Claims, 9 Drawing Sheets

Specification includes a Sequence Listing.

(56) References Cited

FOREIGN PATENT DOCUMENTS

| WO | 2016060935 | A2 | 4/2016 |
| WO | 216118864 | A1 | 7/2016 |
| WO | 2016118840 | A1 | 7/2016 |
| WO | 2016118850 | A1 | 7/2016 |

OTHER PUBLICATIONS

Pranto et al., "Enhancing antimicrobial activity of chitosan films by incorporating garlic oil, potassium sorbate and nisin", LWT—Food Science anti Technology, Academic Press, United Kingdom, vol. 38, No. 8, Dec. 1, 2005, pp. 859-865.

Veerapandian et al., "Analytical and biological characterization of quinazoline semicarbazone derivatives", Med. Chem Res, vol. 19, No. 3, Apr. 23, 2009, pp. 283-298

PCT/US2017/034512, International Search Report and Written Opinion, dated Sep. 20, 2017, 16 pages.

\* cited by examiner

SEQUENCE LISTING

<160> NUMBER OF SEQ ID NOS: 12

<210> SEQ ID NO 1
<211> LENGTH: 20
<212> TYPE: DNA
<213> ORGANISM: Artificial Sequence
<220> FEATURE:
<223> OTHER INFORMATION: 27F-YM Primer

<400> SEQUENCE: 1
agagtttgat ymtggctcag                                              20

<210> SEQ ID NO 2
<211> LENGTH: 20
<212> TYPE: DNA
<213> ORGANISM: Artificial Sequence
<220> FEATURE:
<223> OTHER INFORMATION: 785R Primer

<400> SEQUENCE: 2
actaccrggg tatctaatcc                                              20

<210> SEQ ID NO 3
<211> LENGTH: 25
<212> TYPE: DNA
<213> ORGANISM: Artificial Sequence
<220> FEATURE:
<223> OTHER INFORMATION: NLAB2F Primer

<400> SEQUENCE: 3
ggcggcgtgc ctaatacatg caagt                                        25

<210> SEQ ID NO 4
<211> LENGTH: 25
<212> TYPE: DNA
<213> ORGANISM: Artificial Sequence
<220> FEATURE:
<223> OTHER INFORMATION: WLAB1R Priner

<400> SEQUENCE: 4
tcgctttacg cccaataaat ccgga                                        25

<210> SEQ ID NO 5
<211> LENGTH: 20
<212> TYPE: DNA
<213> ORGANISM: Artificial Sequence
<220> FEATURE:
<223> OTHER INFORMATION: Beta Actin Forward Primer

<400> SEQUENCE: 5
tgacgaggcc cagagcaaga                                              20

<210> SEQ ID NO 6
<211> LENGTH: 20
<212> TYPE: DNA
<213> ORGANISM: Artificial Sequence
<220> FEATURE:
<223> OTHER INFORMATION: Beta Actin Reverse Primer

<400> SEQUENCE: 6

-continued atgggcacag tgtgggtgac                                             20

<210> SEQ ID NO 7
<211> LENGTH: 20
<212> TYPE: DNA
<213> ORGANISM: Artificial Sequence
<220> FEATURE:
<223> OTHER INFORMATION: MIP2 Forward Primer

<400> SEQUENCE: 7
ccccttggtt cagaggatcg                                             20

<210> SEQ ID NO 8
<211> LENGTH: 20
<212> TYPE: DNA
<213> ORGANISM: Artificial Sequence
<220> FEATURE:
<223> OTHER INFORMATION: MIP2 Reverse Primer

<400> SEQUENCE: 8
ttgattctgc ccgttgaggt                                             20

<210> SEQ ID NO 9
<211> LENGTH: 17
<212> TYPE: DNA
<213> ORGANISM: Artificial Sequence
<220> FEATURE:
<223> OTHER INFORMATION: TNF Alpha Forward Primer

<400> SEQUENCE: 9
ggcccgaggc aacacat                                                17

<210> SEQ ID NO 10
<211> LENGTH: 20
<212> TYPE: DNA
<213> ORGANISM: Artificial Sequence
<220> FEATURE:
<223> OTHER INFORMATION: TNF Alpha Reverse Primer

<400> SEQUENCE: 10
gggccatgga actgatgaga                                             20

<210> SEQ ID NO 11
<211> LENGTH: 20
<212> TYPE: DNA
<213> ORGANISM: Artificial Sequence
<220> FEATURE:
<223> OTHER INFORMATION: IL1 Beta Forward Primer

<400> SEQUENCE: 11
ccactgcctt ccctacttca                                             20

<210> SEQ ID NO 12
<211> LENGTH: 20
<212> TYPE: DNA
<213> ORGANISM: Artificial Sequence
<220> FEATURE:
<223> OTHER INFORMATION: IL1 Beta Reverse Primer

<400> SEQUENCE: 12
cagaattgcc attgcacaac                                             20

LACTOBACILLUS AND BACILLUS BASED DIRECT FED MICROBIAL TREATMENT FOR POULTRY AND METHOD OF USE

CROSS-REFERENCE TO RELATED APPLICATIONS

This application claims priority to U.S. Provisional Patent Application No. 62/339,615 filed May 20, 2016, the entirety of which is incorporated by reference herein.

FIELD OF THE DISCLOSURE

This disclosure relates generally to a microbial treatment for poultry. More particularly, the disclosure relates to a direct fed microbial composition including one or more lactic acid bacteria strains in combination with one or more *bacillus* bacteria stains configured to inhibit gastrointestinal pathogens and/or modulate an immune response in a bird. A method of making and method of use are also disclosed herein.

BACKGROUND

Colonization of the gastrointestinal tract by beneficial bacteria in newly hatched broilers and turkey poults is essential for the health of the bird throughout its life (Ballou et al., 2016). Early establishment of lactic acid bacteria (LAB) plays a vital role in stabilizing intestinal homeostasis, digestion and nutrient absorption, detoxification and nurturing mucosal conditions for immunological protection (Oakley and Kogut, 2016).

The inventors have researched the early colonizing microbiota in over 300 day-of hatch chicks from over 11 complexes from five different broiler companies and a greater number of day-old poults from six turkey production companies. The results demonstrate an inconsistent level of total bacteria and specifically lactic acid bacteria leading to a highly variable core gastrointestinal ("GI") microbiome. Research results also indicate a high probability of significant populations of avian pathogenic *Escherichia coli* ("APEC") in broiler chicks and turkey poults at the day-of hatch. The APEC population can disrupt GI homeostasis in the young bird and impact growth and performance. If left unchecked, these isolates can translocate to the blood stream and cause colibacillosis. Colibacillosis infections are of considerable concern for the poultry industry as they are the responsible for high rates of bird death and are the most reported reason for processing rejection (Georgopoulou et al., 2005). Controlling or reducing rates of colibacillosis in the commercial broiler and turkey industry can increase efficiency and productivity that may bare substantial financial impacts to poultry growers.

Conventionally, antibiotics such as in ovo injection of gentamycin has been used to control bacterial challenges such as APEC in the hatchery. However, as poultry companies currently compete for the never antibiotic use ("NAU"), i.e., antibiotic-free, poultry market, alternatives to antibiotics used in the hatcheries are being explored. Probiotics or direct-fed microbials are one of the more viable alternatives given the advancement of the science in recent years and acceptable costs of the products for commercial use.

Accordingly, there is a recognized need for products and methods to impact the colonization of LAB and reduce pathogenic bacterial populations in day-of hatch birds without the use of antibiotics. There is also a recognized need for colonizing the day-of hatch chicks with LAB that can aid in developing intestinal mucosa and gut-associated lymphoid tissue critical for immunological protection. There is also a recognized need for products and methods that provide a competitive environment to exclude or reduce the APEC populations in the day-of hatch birds.

BRIEF SUMMARY

The inventors have developed a direct fed microbial composition that can increase the presence of lactic acid bacteria and *Bacillus* bacteria and inhibit pathogenic bacterial populations in the gastrointestinal tracts of birds.

In one aspect of the invention, a direct fed microbial composition is provided including an isolated *Lactobacillus* strains and an isolated *Bacillus* strains, wherein the composition inhibits at least one avian pathogenic *Escherichia coli*, *Clostridium perfringens* and Enterobacteriaceae in a gastrointestinal tract of a bird having ingested an effective amount of said direct fed microbial composition.

In some embodiments the composition includes one or more isolated *Lactobacillus* strains chosen from at least one of strains *Lactobacillus plantarum* Lp-115 and *Lactobacillus salivarius* Ls-33.

In some embodiments the composition includes one or more isolated *Bacillus* strains chosen from at least one of strains 747, 967, 1104, 1145, 1541, 1781, 1999 and 2018.

In some embodiments the composition is configured to inhibit at least one pathogen chosen from avian pathogenic *Escherichia coli*, *Clostridium perfringens* and Enterobacteriaceae in the gastrointestinal tract of a bird.

In another aspect of the invention, the composition may inhibit avian pathogenic *Escherichia coli* in the gastrointestinal tract of a bird at least 12 days after a day-of hatch, wherein the bird ingested the effective amount of said direct fed microbial composition on the day-of hatch of the bird.

In another aspect of the invention, the composition may inhibit avian pathogenic *Escherichia coli* in the gastrointestinal tract of the bird, wherein the bird received in ovo gentamycin prior to ingesting the effective amount of said direct fed microbial composition.

In another aspect of the invention, the composition may reduce avian pathogenic Enterobacteriacaea in the gastrointestinal tract of the bird at least 1 day after a day-of hatch, wherein the bird ingested the effective amount of said direct fed microbial composition on the day-of hatch of the bird.

In another aspect of the invention, the composition may reduce avian pathogenic *Escherichia coli* in the gastrointestinal tract of the bird at least 1 day after a day-of hatch.

In another aspect of the invention, the isolated *Bacillus* strain and the isolated *Lactobacillus* strain comprise the predominant bacteria in the gastrointestinal tract of the bird at least 1 day after a day-of hatch, wherein the bird ingested the effective amount of said direct fed microbial composition on the day-of hatch of the bird.

In some embodiments the composition further comprises a cryoprotectant disposed about the isolated *Bacillus* strain, wherein the isolated *Bacillus* strain is a powdered lyophilized isolated *Bacillus* strain.

In some embodiments the composition further comprises a cryoprotectant disposed about the isolated *Lactobacillus* strain, and wherein said isolated *Lactobacillus* strain is a powdered lyophilized isolated *Lactobacillus* strain.

In some embodiments the composition further comprises a water soluble carrier.

In some embodiments the composition is wetted.

In some embodiments the wetted composition is a gel or similar high viscosity liquid.

In some embodiments the composition further comprises a color agent or color attractant configured to induce ingestion of the composition by a bird.

In another aspect of the invention, a method for colonizing day-of hatch birds with lactic acid bacteria and *Bacillus* bacteria is disclosed.

In some embodiments, the method includes the steps of developing intestinal mucosa and gut-associated lymphoid tissue providing immunological protection.

In another aspect of the invention, inventors have developed a composition of lactic acid bacteria with *Bacillus* strains capable of controlling the growth of the APEC population.

In some embodiments, administration of the compositions results in reduced incidence of disease and improve the bird performance without the use of antibiotics.

In another aspect of the invention, administration of the compositions results in inhibition of a pathogen chosen from at least one of *Escherichia coli, Clostridium perfringens* and Enterobacteriaceae in the one or more birds.

In another aspect of the invention, administration of the compositions results in decreasing a mortality rate of one or more birds.

In another aspect of the invention, administration of the compositions may result in improving the coefficient of variation of weight of the one or more birds.

In another aspect of the invention, administration of the compositions may result in reducing the occurrence of necrotic enteritis in the one or more birds.

In another aspect of the invention, administration of the compositions may result in reducing the occurrence of colibacillosis in the one or more birds.

In another aspect of the invention, administration of the compositions may result in modulating immune responses of inflammatory cytokines in gastrointestinal epithelial cells in the one or more birds.

In another aspect of the invention, administration of the compositions comprising isolated *Lactobacillus salivarius* Ls-33 results in amelioration of the gastrointestinal inflammatory cytokine response associated with a gram negative bacterial infection in the gastrointestinal tract of the one or more birds.

Such methods are outlined in more detail in the examples below.

Other objects, features and advantages of the present invention will become apparent after review of the specification, claims and drawings.

DETAILED DESCRIPTION

I. General

Figure 1:
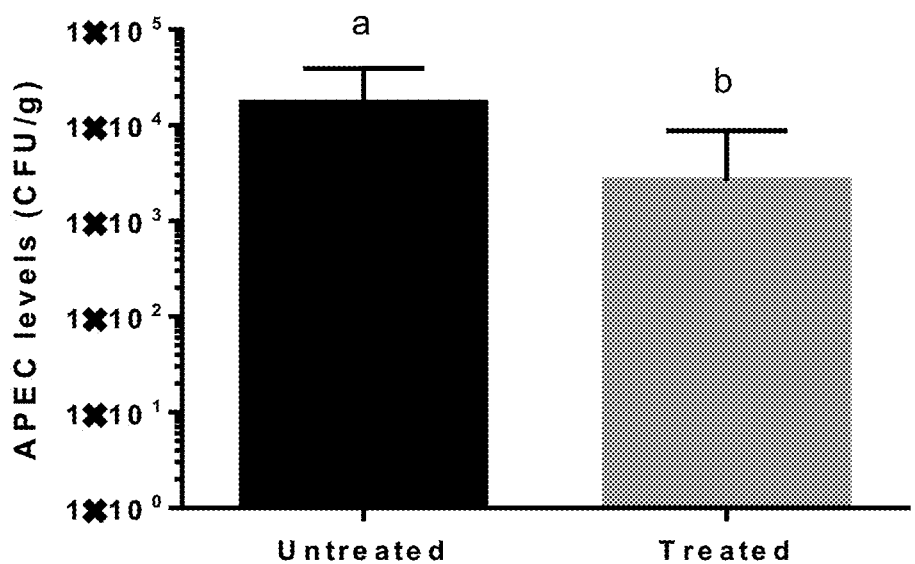
FIG. 1 is a graph showing the average level of APEC (CFU/g) with standard deviation in both an untreated group and a group treated with a composition in accordance with one embodiment of the present invention, pursuant to Example 1.

It is understood that this disclosure is not limited to the particular methodology, protocols, materials, and reagents described, as these may vary. The terminology used herein is for the purpose of describing particular embodiments only, and is not intended to limit the scope of the present invention.

As used herein and in the appended claims, the singular forms "a", "an", and "the" include plural reference unless the context clearly dictates otherwise. As well, the terms "a" (or "an"), "one or more" and "at least one" can be used interchangeably herein. The terms "comprising" and variations thereof do not have a limiting meaning where these terms appear in the description and claims. Accordingly, the terms "comprising", "including", and "having" can be used interchangeably.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. All publications and patents specifically mentioned herein are incorporated by reference in their entirety for all purposes including, for example, describing and disclosing chemicals, cell lines, vectors, animals, instruments, statistical analyses, and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

The numerical ranges in this disclosure are approximate, and thus may include values outside of the range unless otherwise indicated. Numerical ranges include all values from and including the lower and the upper values, in increments of one unit, provided that there is a separation of at least two units between any lower value and any higher value.

As used herein, the term "animal" includes but is not limited to human, mammal, amphibian, bird, reptile, pigs, cows, cattle, goats, horses, sheep, poultry, and other animals kept or raised on a farm or ranch, sheep, big-horn sheep, buffalo, antelope, oxen, donkey, mule, deer, elk, caribou, water buffalo, camel, llama, alpaca, rabbit, mouse, rat, guinea pig, hamster, ferret, dog, cat, and other pets, primate, monkey, ape, and gorilla. In some embodiments, the animals are poultry, birds or avian, including but not limited to chicken and turkey.

By "at least one strain," is meant a single strain but also mixtures of strains comprising at least two strains of bacteria. By "a mixture of at least two strains," is meant a mixture of two, three, four, five, six or even more strains. In some embodiments of a mixture of strains, the proportions can vary from 1% to 99%. When a mixture comprises more than two strains, the strains can be present in substantially equal proportions in the mixture or in different proportions.

As used herein, the term "feed" refers to a liquid or a solid feed. The feed may include a commercial feed. Feeds may be blended from various raw materials and additives. These blends are formulated according to the specific requirements of the target animal.

As used herein, "effective amount" is meant a quantity of one or more strains and/or the combination thereof to improve performance of an animal. Improvement in performance can be measured as described herein or by other methods known in the art. An effective amount can be administered to the animal by providing ad libitum access to feed containing the strain and/or the combination thereof. The strain and/or the combination thereof can also be administered in one or more doses. In one embodiment of the present invention, the composition may provide an effective amount wherein the a direct fed microbial composition ingested by the bird per day comprises a concentration of an isolated $Bacillus$ strain of between about $2.5 \times 10^7$ CFU/bird and about $1.0 \times 10^9$ CFU/bird. In one embodiment of the present invention, the composition may provide an effective amount wherein the a direct fed microbial composition ingested by the bird per day comprises a concentration of an isolated $Lactobacillus$ strain of between about $2.5 \times 10^7$ CFU/bird and about $1.0 \times 10^9$ CFU/bird.

As used herein, "performance" refers to the productivity of an animal, such as a poultry, measured by one or more of the following parameters: mortality, number of offspring born, number of offspring born alive, offspring birth weight, survivability, immune system function, inflammation, feed conversion, coefficient of variation of weight, occurrence of necrotic enteritis, occurrence of colibacillosis, and response of inflammatory cytokines in gastrointestinal epithelial cells. "An improvement in performance" or "improved performance" as used herein, refers to an improvement in at least one of the parameters listed under the performance definition.

II. Description of a Preferred Embodiment

Administration of the composition in accordance with one embodiment of the present invention, including a combination of one or more lactic acid bacteria (LAB) in combination with one or more $Bacillus$ microorganisms to poultry may be accomplished by several methods including spraying the rehydrated bacteria in water or a gel onto the birds via a spray aerosol through use of a spray cabinet in the hatchery, adding the combination LAB and $Bacillus$ strains to the birds' feed, or drinking water via a proportioner and diluted into the water lines for delivery via the nipple drinkers, or to the bedding or nest box of the hens so as to be transferred from the hens to the eggs or via in ovo injection into the eggs.

The lactic acid bacteria described herein were selected from the commercially available strains that matched the predominant LAB species found in the core microbiome of the turkey poults and broiler chicks. Strains were selected based on their immunological function so as to contribute to the development of the innate and acquired immune system and control inflammation. A cell culture assays using the rat intestinal epithelial cell line IEC6, was performed to screen candidate microbial organisms and their combinations in an inflammatory model with $E.\ coli$ lipopolysaccharide (LPS) as the source of inflammation. Candidate strains were screened in the cell culture assay to determine changes in inflammatory cytokine gene expression with the presence and absence of LPS inflammatory stimulation. The expression of inflammatory cytokine genes (ex., TNF-$\alpha$, MIP-2, IL-1$\beta$, IL-6, and IL-17) were measured using qPCR to determine fold-changes in gene expression associated with candidate bacterial strains. Strains were selected for their propensity to decrease the inflammatory cytokine gene expression in the IEC6 cells associated with LPS exposure.

The *Bacillus* strains described herein were selected based on their inhibition patterns against known APEC isolates from the day-of hatch broiler and turkey poults gastrointestinal tracts. *Bacillus* strains that inhibited the representative members from the clusters of the pathogenic APEC bacteria were selected. For this, the *Bacillus* strains were each grown up and a cell-free supernatant was produced. The APEC isolates representing the diversity in the GI tract of the day-of hatch birds were grown up and used as indicator organisms for an inhibition assay. Aliquots of bacteriocin from each *Bacillus* strain were added to the growth media for each APEC isolate. Positive controls containing only the indicator isolate and negative controls containing fresh medium to confirm bacteriocin sterility were also included. After incubation, the OD of each well were read and the results were expressed as percent inhibition of each APEC by each *Bacillus*.

*Bacillus* strains were also selected based on additional characteristics including the production of extracellular enzymes, such as proteases, amylases, and cellulose and the ability to modulate the gastrointestinal microbial communities. The changes in the gastrointestinal communities associated with feeding *Bacillus* strains has been characterized using molecular DNA techniques.

LAB strains identified that matched the predominant LAB species found in the core microbiome of the turkey poults and broiler chicks and were shown immunologically to contribute to the development of the innate and acquired immune system and control inflammation include *Lactobacillus plantarum* Lp-115 and *Lactobacillus salivarius* Ls-33, both of which are considered within the scope of the present invention. These strains can be fed individually or in combination with each other and/or in combination with *Bacillus* strains. They can be applied at the hatchery via water or gel through the spray cabinet or at the farm via the water line or into the feed.

*Bacillus* strains identified as being useful against APEC poultry pathogens include strains 747, 1104, 1541, 1781 and 2018, all of which are considered within the scope of the present invention. These strains can be fed individually or in combination with each other or in the preferred embodiment in combination with LAB strains. Other *Bacillus* strains are also included within the scope of the invention include strains 967, 1145 and 1999, all of which are considered within the scope of the present invention. These strains can be fed individually or in combination with each other and LAB strains. They can be applied at the hatchery via water or gel through the spray cabinet or at the farm via the water line or into the feed. The *Bacillus* strains described below in the subsequent examples are non-limiting examples of *Bacillus* strains considered within the scope of the present invention, which may include strains 747, 967, 1104, 1145, 1541, 1781, 1999, 2018, and combinations thereof. *Bacillus* strains 747. 1104, 1541, 1781 and 2018 were deposited on May 24, 2016 at the Agricultural Research Service Culture Collection (NRRL), 1815 North University Street. Peoria, Ill., 61604 and given accession numbers NRRL B-67257 for strain *B. subtilis* 747, NRRL B-67258 for strain *B. subtilis* 1104, NRRL B-67260 for strain *B. subtilis* 1541, NRRL B-67259 for strain *B. subtilis* 1781 and NRRL B-67261 for strain *B. subtilis* 2018. Strain *B. subtilis* 1999 was deposited on Sep. 15, 2016 and given the accession number NRRL B-67318. All deposits were made under the provisions of the Budapest Treaty on the International Recognition of the Deposit of Microorganisms for the Purposes of Patent Procedure.

The *Bacillus* strains are grown in a liquid broth containing protein, carbohydrates and minerals at a constant temperature and agitation to maximize the initial cell density. In the initial phase of the fermentation, the conditions are set to maximize the cell density and then in the later stages of the fermentation conditions are set to convert the cells to spores. In a preferred embodiment, the strains are grown to an initial OD in Nutrient broth where the cell yield is at least $2 \times 10^9$ colony forming units (CFU) per ml of culture. Following the initial growth phase, agitation can be reduced, supplements added to induce sporulation and the cells convert to spore forms. Once the culture reaches a maximum spore density, the culture is harvested by separating the cells from the medium by centrifugation. Wet spore paste is then mixed with stabilizing agents such as starch, maltodextrin, citric acid and cryoprotectants if the paste is to be freeze-dried. The suspended spore paste is then freeze-dried and milled or spray dried to provide a flowable powder.

The lactic acid bacteria strains are grown in a liquid broth containing hydrolyzed proteins, simple carbohydrates and mineral salts at a constant temperature and agitation and under pH control to maximize the cell density. In a preferred embodiment, the strains are grown to an initial OD in a commercial broth medium where the cell yield is at least $5 \times 10^9$ colony forming units (CFU) per ml of culture. Once the culture reaches a maximum cell density, the culture is treated with a sub-lethal heat shock or equivalent treatment to induce stress response proteins that provide the cells with additional stability. After this treatment, cells are separating from the spent growth medium by centrifugation. The wet cell paste is then mixed with stabilizing agents such as starch, maltodextrin and cryoprotectants along with mineral slats of magnesium and manganese buffers to coat the cells with a protecting layer that once freeze-dried will become a hard coating. This coating will protect the cells from moisture and keep the cells in a dried and stable form. The slurry cell suspension is dropped into liquid nitrogen to form pellets and stored at $-20°$ C. until freeze-drying. The frozen pellets are then freeze-dried and milled to provide a flowable culture powder.

To prepare compositions, the dried *Bacillus* spore powder can be combined with the freeze-dried LAB culture powder and added to a water-soluble carrier such as whey, maltodextrin or sucrose or a dried gel material such as in a ribbon mixer and mixed to get an even distribution of the spores in the carrier. The components are blended such that a uniform mixture of the carrier and cultures result.

The count of the bacteria is important when combined with a carrier. At the time of manufacture of the composition for the day-of hatch application, the *Bacillus* count provides at least $2.5 \times 10^7$ CFU/bird and the LAB count provides at least $2.5 \times 10^8$ CFU/bird. The counts may be increased to as high as $1.0 \times 10^8$ CFU/bird for the *Bacillus* and $1.0 \times 10^9$ CFU/bird for the LAB from the base numbers and still have complete efficacy.

At the time of manufacture of the composition for the water or feed application, the *Bacillus* count provides at least $2.5 \times 10^8$ CFU/bird and the LAB count provides at least $2.5 \times 10^7$ CFU/bird. The counts may be increased to as high as $1.0 \times 10^9$ CFU/bird for the *Bacillus* and $1.0 \times 10^8$ CFU/bird for the LAB from the base numbers and still have complete efficacy.

CFU or colony forming unit is the viable cell count of a sample resulting from standard microbiological plating methods. The term is derived from the fact that a single cell when plated on appropriate medium will grow and become a viable colony in the agar medium. Since multiple cells may give rise to one visible colony, the term colony forming unit is a more useful unit measurement than cell number.

To prepare compositions, the cultures and the carrier can be added to a ribbon or paddle mixer and mixed preferably for about 15 minutes. The components are blended such that a uniform mixture of the carrier and cultures result. The final product is preferably a flowable powder.

In one embodiment, the combination LAB and *Bacillus* strains may be administered as a gel application where the bacteria, gums, hydrocolloids, stabilizers and color attractant form non-uniform droplets, and cling promotes preening and chick's droplet consumption. Contents of the dry powder (10,000 doses per scoop) is dissolved in 2.0 L of cool water. This is mixed with a hand-held blender and administer topically by spray at 1 day of age (hatch day) or at placement at 20 mL (0.71 ounces) for every 100 birds through a gel-spray cabinet machine or device.

The following examples are offered for illustrative purposes only, and are not intended to limit the scope of the present invention in any way. Indeed, various modifications of the invention in addition to those shown and described herein will become apparent to those skilled in the art from the foregoing description and the following examples and fall within the scope of the appended claims.

III. Examples

Example 1: The Effect of a Lactic Acid Bacteria/*Bacillus* Product, According to One Embodiment of the Present Invention, on Avian Pathogenic *E. coli* and *Clostridium perfringens* Levels in the Gastrointestinal Tract of Young Broiler Chicks A. Introduction The first moments of life are crucial to a young broiler's development of a balanced and healthy microbiome (Stanley et al., 2014). Microbes from the environment make their way into the newly exposed gastrointestinal tract (GIT) of the chick and begin to occupy niches and compete for resources (Pedroso et al., 2005; Ranjitkar et al., 2016; Stanley et al., 2014). These early colonizing bacteria set the stage for immune function, bacterial homeostasis and nutritional processing for the duration of the bird's life (Bar-Shira and Friedman, 2006; Danzeisen et al., 2013; Konsak et al., 2013; Stanley et al., 2012; Yin et al., 2009). All of these factors contribute to the efficiency and profitability of various poultry industries. In today's ultra-sanitized broiler production systems, newly-hatched chicks are passively inoculated by organisms from the bird's immediate environment (Stanley et al., 2014). With sterilization as the main goal, sanitation methods give little consideration to the retention or introduction of beneficial microorganisms after sanitation is complete, and since total sterilization is nearly impossible, those microbes that do persist vary in number and taxa. This means that microbial levels and compositions in the bird's GIT are often irregular and populated with undesirable organisms such as avian pathogenic *Escherichia coli* (APEC) and *Clostridium perfringens*.

APEC is a causative agent for colibacillosis in birds in the form of airsacculitis, cellulitis, pericarditis, and perihepatitis (Barnes H J et al., 2008). Colibacillosis infections are of considerable concern for the poultry industry as they are responsible for high rates of bird death and are the most reported reason for processing rejection (Georgopoulou et al., 2005). *C. perfringens* strains that produce alpha toxin are categorized as the *C. perfringens* Type A toxinotype and cause necrotic enteritis in poultry which increases mortality and reduces weight gain (Songer, 1996). Enteric pathogens, especially APEC and *C. perfringens*, are of great importance to broiler producers and decreasing their disease instances is highly desirable. This can be achieved by reducing pathogen levels in the GIT by direct inhibition through exposure to antimicrobial compounds and by competitive exclusion of pathogens and immune modulation by probiotic microorganisms (La Ragione et al., 2001).

In this embodiment, the product in accordance with one aspect of the present invention, is a gel-based direct fed microbial, applied in a hatchery, designed to deliver two pathogen-inhibiting *Bacillus* strains and an immune-strengthening *Lactobacillus salivarius* to freshly hatched chicks. Members of the genus *Bacillus* are known to produce a diverse and strain-specific array of antimicrobial compounds known as bacteriocins (Tagg et al., 1976). The inventors have screened and isolated two strains of *Bacillus* that show a strong inhibitory effect on APEC and *C. perfringens*. These strains comprise 10% of the microbial components of the product, in accordance with one embodiment of the present invention. The remaining 90% of the microbial formulation is made up of Ls-33, a strain of *Lactobacillus salivarius* which exhibits various beneficial immune modulation functions.

An in vivo study was designed to measure the effect of the product, in accordance with this embodiment of the present invention, on the microbial pathogen load of 7 day old chicks. The GITs of week old birds treated with the product, in accordance with this embodiment of the present invention, (referred to herein as "treated") and those untreated, i.e., without the product, in accordance with this embodiment of the present invention, (referred to herein as "untreated"), consisting of 10 birds per group, were sampled for APEC and *C. perfringens* type A levels. Inventors' data shows that treated birds saw a reduction in APEC and *C. perfringens* type A levels when compared to the control group of untreated birds.

B. Materials and Methods

Design: Gastrointestinal tracts (GIT) were collected from 7-day old broiler chicks from a southwestern US commercial broiler company. Sampling consisted of 10 GITs that had been treated with the product, in accordance with this embodiment of the present invention, at the hatchery via spray cabinet application within 18 hours of hatch, and 10 GITs that were not treated with the product, in accordance with this embodiment of the present invention.

*Bacillus*/*Lactobacillus* combination product: The microbial components of the product, in accordance with this embodiment of the present invention, were comprised of three bacterial strains; *Bacillus* 1104 (5%), *Bacillus* 1781 (5%) and *L. salivarius* Ls-33 (90%). The product was applied at the hatchery to newly hatched chicks via a spray cabinet.

Processing of Gastrointestinal Tracts: Selected broilers were sacrificed and the gastrointestinal tracts from the duodenal loop to the cloaca were removed and transported in sterile Whirl-pak® bags (B01297, Nasco, Fort Atkinson, Wis.) on ice. Upon arrival, 10 cm sections of the duodenum, jejunum, and ilium were rinsed with ~5 mL sterile 0.1% Bacto™ Peptone (Becton, Dickinson and Company, Sparks, Md.) broth, cut longitudinally, and combined in a sterile, filtered Whirl-pak® bag (B01348, Nasco, Fort Atkinson, Wis.). 99 mL of sterile 0.1% peptone was added to the bag then the sections were masticated at 300 rpm, for 1 min in a Stomacher (Model 400 circulator, Seward, England). Serial dilutions were made and pour plated in duplicate with both CHROMagar™ ECC to enumerate *E. coli*, and *perfringens* TSC agar base (Oxoid™) with D-cycloserine (Sigma, 400 mg/L) for *Clostridium* spp. enumeration. APEC Screening: Typical *E. coli* colonies on CHROMagar™ appear blue. After 12-24 h of incubation at 37° C., all blue colonies were counted and recorded as presumptive APEC CFU/g counts. Five isolated blue colonies from each bird were picked and enriched in TSB (Becton, Dickenson & Company) if possible. Genomic DNA was extracted from each isolate using the following gDNA extraction method: Add 20 µL of lysozyme (100 mg/mL) to 500 µL of overnight growth in TSB and incubate at 37° C. for 30 min, add 300 µL of lysis buffer (6 M Guanidine, 20% Triton-X 100, 10 mM Tris-HCl, pH 7.5) and incubate at 25° C. for 15 min, add 20 µl of Protease K (NEB, 800 U/ml) and incubate at 55° for 30 min, transfer 400 µL of lysate to a Wizard® SV 96 Binding Plate from Promega and continue with manufacturer's filtration instructions from Promega Wizard® SV 96 Genomic DNA Purification System starting from step 3.C.4 (April 2015 revision).

APEC pathotype was determined using multiplex polymerase chain reaction (PCR). In order to be considered APEC, an *E. coli* isolate had to contain at least two of the five following APEC-associated virulence genes in its genome: hlyF, ompT, iroN, iss, iutA (Johnson et al., 2008). Each reaction mixture contained 4 mM magnesium chloride (Invitrogen), 0.25 mM deoxynucleoside triphosphates (Invitrogen), 0.25 µM each primer (Eurofins), and 1 U Platinum® Taq DNA Polymerase (Invitrogen) and 5 µL of template gDNA (Johnson et al., 2008). The reaction was run on an Applied Biosystems Veriti® Thermal Cycler with the following protocol: 94° C. for 2 min; 25 cycles of 94° C. for 30 s, 63° C. for 30 s, 68° C. for 3 min; and a final cycle of 72° C. for 10 min. The PCR product was then run though capillary gel electrophoresis using a Fragment Analyzer™ from Advance Analytical Technologies, Inc. and visualized on PROsize 2.0 (Advance Analytical Technologies, Inc.).

*C. perfringens* Type A Screening: Presumptive *C. perfringens* isolates appear black on *perfringens* TSC agar base. All black colonies were counted and recorded as presumptive *C. perfringens* CUF/g counts. Five isolated black colonies from each bird were picked and grown in RCM broth (Oxoid™) if possible. Genomic DNA was extracted from each isolate using the Roche Applied Science High Pure PCR Template Kit.

*C. perfringens* toxinotype was determined using polymerase chain reaction (PCR) to amplify the alpha toxin gene. In order for an isolate to be considered *C. perfringens* Type A it had to contain the alpha toxin gene, otherwise it was categorized as a non *perfringens Clostridium* species. Each reaction mixture contained 2.5 µL 10×PCR buffer (Invitrogen), 1.6 µL magnesium chloride (Invitrogen), 0.5 µL deoxynucleoside triphosphates (Invitrogen), 100 pmol primers (Eurofins), and 1 U Platinum® Taq DNA Polymerase (Invitrogen) and 2 µL of template gDNA, 7.8 µL of ddH$_2$O (Yoo et al., 1997). The reaction was run on an Applied Biosystems Veriti® Thermal Cycler with the following protocol: 5 min at 94° C., followed by 30 incubation cycles consisting of 1 min at 55° C., 1 min at 72° C., and 1 min at 94° C. The PCR product was then run though capillary gel electrophoresis using a Fragment Analyzer™ from Advance Analytical Technologies, Inc. and visualized on PROsize 2.0 (Advance Analytical Technologies, Inc.).

Counts and Statistics: Pathotype levels for each bird were determined by multiplying the weight-adjusted presumptive CFU/g counts by the percent of presumptive isolates from each bird that were revealed to be pathogenic (*C. perfringens* or APEC). Birds that did not produce any detectable colonies on agar plates or birds that did not produce any confirmed pathogens though screening were assigned a value of <500 CFU/g for APEC and <50 CFU/g for *C. perfringens* (for calculations this value was entered as 500 CFU/g and 50 CFU/g, respectively).

Statistical analysis for the comparison of untreated vs treated birds was run using a Mann-Whitney t-test on the log$_{10}$ transformed counts. Significant difference threshold was set at $p<0.05$.

C. Results

Figure 2:
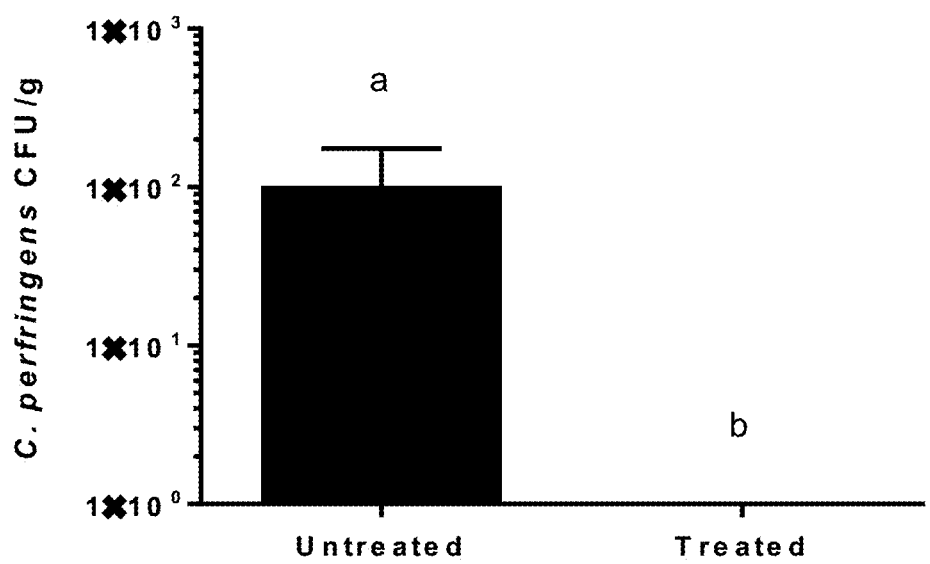
FIG. 2 is a graph showing the average level of *Clostridium perfringens* type A (CFU/g) with standard deviation in both an untreated group and a group treated with a composition in accordance with one embodiment of the present invention, pursuant to Example 1.

The average APEC and *C. perfringens* levels by treatment group are represented in CFU/g or tissue are shown in FIGS. 1 and 2. Control birds harbored an average APEC level of $1.7 \times 10^4$ CFU/g, which was significantly higher than the $2.6 \times 10^3$ CFU/g APEC level in the treated birds. Additionally, *C. perfringens* levels in the GITs of untreated birds were significantly higher than in the treated birds with average counts of $1.0 \times 10^2$ CFU/g and <10 CFU/g, respectively.

D. Discussion

These data demonstrate significant reduction of APEC and *C. perfringens* levels in young broilers that had been treated with the product, in accordance with this embodiment of the present invention. Reduction of these pathogens can diminish cases of disease in broilers such as colibacillosis and necrotic enteritis, diseases which present significant financial liability to the poultry industry. Inventors' research shows that including the inventors' DFM product in feed is effective in reducing APEC and *C. perfringens* prevalence in young broilers, therefore decreasing the disease-burden in commercial broiler operations and improving yields.

Example 2: The Effect of a Lactic Acid Bacterial *Bacillus* Combination Product, According to One Embodiment of the Present Invention, on the Early Gastrointestinal Pathogen Load of Broilers in a Commercial Operation A. Introduction Initial colonization of beneficial bacteria in the gastrointestinal tract in newly hatched broilers is essential for the health of the bird throughout its life (Ballou et al., 2016). Early establishment of lactic acid bacteria (LAB) plays a vital role in stabilizing intestinal homeostasis, digestion and nutrient absorption, and nurturing mucosal conditions for immunological protection (Brisbin et al., 2010, 2011; Haghighi et al., 2006; Yin et al., 2009).

Avian pathogenic *Escherichia coli* (APEC) can have significant negative ramifications on the productivity of commercial broiler operations. APEC is a causative agent for colibacillosis in birds in the form of airsacculitis, cellulitis, pericarditis, or perihepatitis (Barnes H J et al., 2008). Although APEC cause diseases that is outside the gastrointestinal tract, the GI tract is an important reservoir for APEC isolates. Recently, inventors' research has documented significant populations of APEC in broiler chicks at the day-of hatch. A high population of APEC can disrupt GI homeostatis in the young bird and impact early growth and performance. If left unchecked, these isolates can translocate to blood stream and cause colibacillosis.

Colibacillosis infections are of considerable concern for the poultry industry as they are the responsible for high rates of bird death and are the most reported reason for processing rejection (Georgopoulou et al., 2005). Controlling or reducing rates of colibacillosis in the commercial broiler industry can increase efficiency and productivity which may bare substantial financial impacts to poultry growers. Conventionally, antibiotics such as in ovo injection of gentamycin has been used to control APEC in the hatchery (Nascimento and Nascimento, 1994). However, today as poultry companies compete for the never antibiotic use (NAU), i.e., antibiotic-free, poultry meat market alternatives to antibiotics are being explored.

Colonizing the day-of hatch chicks with LAB that can aid in developing intestinal mucosa and gut-associated lymphoid tissue critical for immunological protection (Brisbin et al., 2010, 2011; Haghighi et al., 2006). Combining these LAB with *Bacillus* strains capable of producing bacteriocins against APEC in a day-of hatch application should be an important step in reducing APEC disease and improving performance without the use of antibiotics. The purpose of this trial was to determine if the combination of LAB and *Bacillus* to a day-of hatch bird would reduce APEC populations and to determine if the LAB/*Bacillus* combination would be effective with and without gentamycin.

B. Materials and Methods.

A commercial broiler complex in Virginia with a single hatchery and multiple production farms was the site for the trial. The complex produced over 1 million birds per week. Selected eggs were injected at the hatchery with gentamycin at full or ½ or no dose and selected birds were treated with the product, in accordance with this embodiment of the present invention, comprising a commercial blend of LAB and *Bacillus* strains via gel delivery system at the day-of hatch (referred to herein as "treated"). The microbial components of the product, in accordance with this embodiment of the present invention, were comprised of three bacterial strains; *Bacillus* 1104 (5%), *Bacillus* 1781 (5%) and *L. salivarius* Ls-33 (90%). Each treatment was run for one week and the birds were tracked by treatment to the production farms. The treatments included following:

Gentamycin/Not treated with the product, in accordance with this embodiment of the present invention.

½ dose Gentamycin/Treated with the product, in accordance with this embodiment of the present invention.

No Gentamycin/Not treated with the product, in accordance with this embodiment of the present invention.

No Gentamycin/Treated with the product, in accordance with this embodiment of the present invention.

Birds were collected from the production farms at 12-15 days of age, euthanized and the GI tracts sent to the laboratory for analysis of APEC populations. All samples were coded so as not to disclose the treatments until the completion of the trial.

Processing of Gastrointestinal Tracts: Ten birds randomly picked from the production farms for each treatment were sacrificed and the gastrointestinal tracts from the duodenal loop to the cloaca were removed and transported in sterile Whirl-pak® bags (B01297, Nasco, Fort Atkinson, Wis.) on ice. Upon arrival, 10 cm sections of the duodenum, jejunum, and ilieum were rinsed with ~5 mL sterile 0.1% Bacto™ Peptone (Becton, Dickinson and Company, Sparks, Md.) broth, cut longitudinally, and combined in a sterile, filtered Whirl-pak® bag (B01348, Nasco, Fort Atkinson, Wis.). 99 mL of sterile 0.1% peptone was added to the bag then the sections were masticated at 300 rpm, for 1 min in a Stomacher (Model 400 circulator, Seward, England). Serial dilutions were made and pour plated in duplicate with both CHROMagar™ ECC to enumerate *E. coli*, and *perfringens* TSC agar base (Oxoid™) with D-cycloserine (Sigma, 400 mg/L) for *Clostridium* spp. enumeration.

APEC Screening: Typical *E. coli* colonies on CHROMagar™ appear blue. After 12-24 h of incubation at 37° C., all blue colonies were counted and recorded as presumptive APEC CFU/g counts. Five isolated blue colonies from each bird were picked and enriched in TSB (Becton, Dickenson & Company), if possible. Genomic DNA was extracted from each isolate using the following gDNA extraction method: Add 20 µL of lysozyme (100 mg/mL) to 500 µL of overnight growth in TSB and incubate at 37° C. for 30 min, add 300 µL of lysis buffer (6 M Guanidine, 20% Triton-X 100, 10 mM Tris-HCl, pH 7.5) and incubate at 25° C. for 15 min, add 20 µl of Protease K (NEB, 800 U/ml) and incubate at 55° for 30 min, transfer 400 µL of lysate to a Wizard® SV 96 Binding Plate from Promega and continue with manufacturer's filtration instructions from Promega Wizard® SV 96 Genomic DNA Purification System starting from step 3.C.4 (April 2015 revision).

APEC pathotype was determined using multiplex polymerase chain reaction (PCR). In order to be considered APEC, an *E. coli* isolate had to contain at least two of the five following APEC-associated virulence genes in its genome: hlyF, ompT, iroN, iss, iutA (Johnson et al., 2008). Each reaction mixture contained 4 mM magnesium chloride (Invitrogen), 0.25 mM deoxynucleoside triphosphates (Invitrogen), 0.25 µM each primer (Eurofins), and 1 U Paltinum® Taq DNA Polymerase (Invitrogen) and 5 µL of template gDNA (Johnson et al., 2008). The reaction was run on an Applied Biosystems Veriti® Thermal Cycler with the following protocol: 94° C. for 2 min; 25 cycles of 94° C. for 30 s, 63° C. for 30 s, 68° C. for 3 min; and a final cycle of 72° C. for 10 min. The PCR product was then run though capillary gel electrophoresis using a Fragment Analyzer™ from Advance Analytical Technologies, Inc. and visualized on PROsize 2.0 (Advance Analytical Technologies, Inc.).

Counts and Statistics: Pathotype levels for each bird were determined by multiplying the weight-adjusted presumptive CFU/g counts by the percent of presumptive isolates from each bird that were revealed to be pathogenic (APEC). Birds that did not produce any detectable colonies on agar plates or birds that did not produce any confirmed pathogens though screening were assigned a value of <10 CFU/g for APEC or zero for the analysis.

Statistical analysis for the comparison of untreated vs treated birds was run using a Mann-Whitney t-test. Significant difference threshold was set at $P<0.05$.

C. Results.

Figure 3:
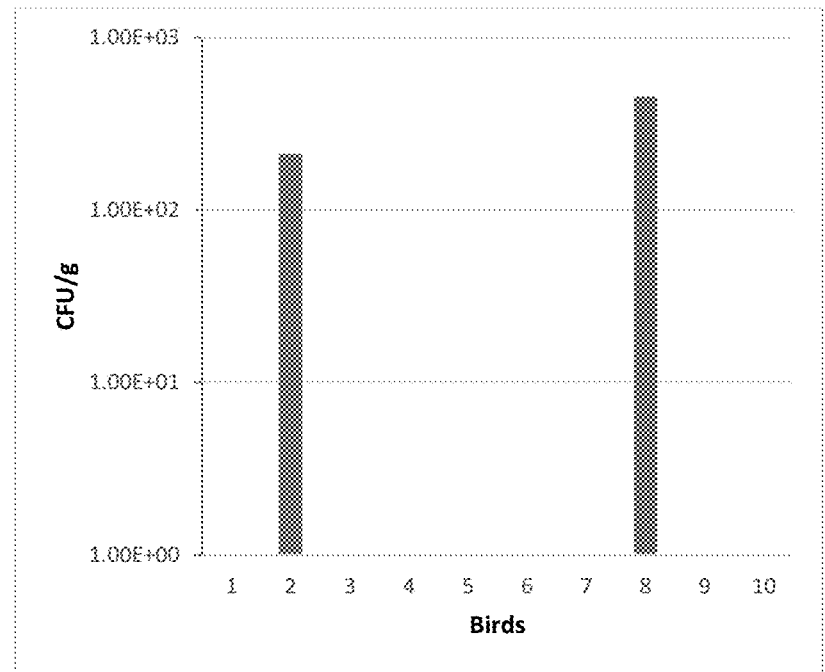
FIG. 3 is a graph showing APEC levels (CFU/g) in the GI tract of ten birds injected with gentamycin and not treated with a composition in accordance with one embodiment of the present invention, pursuant to Example 2.
Figure 4:
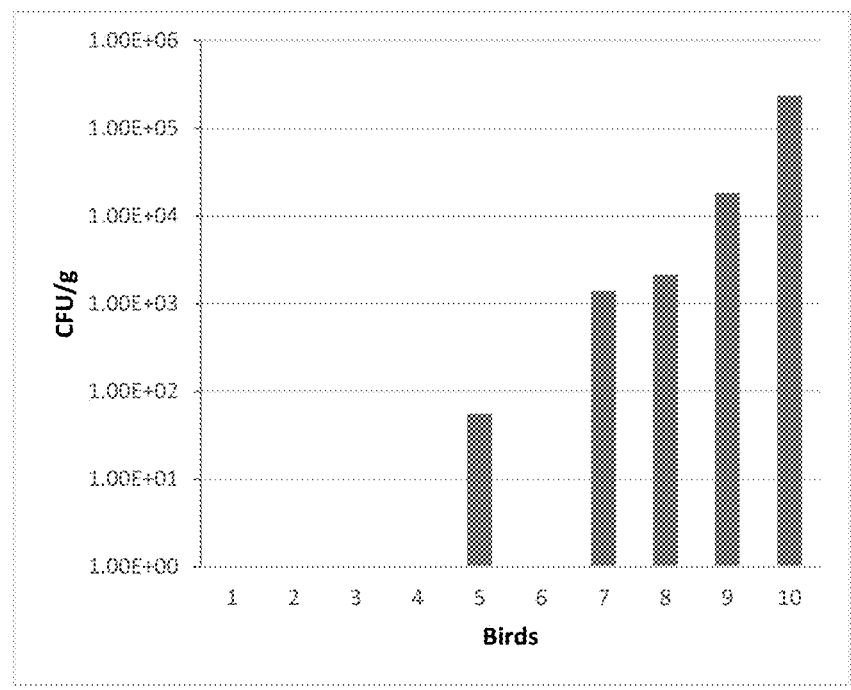
FIG. 4 is a graph showing APEC levels (CFU/g) in the GI tract of ten birds not injected with gentamycin and not treated with a composition in accordance with one embodiment of the present invention, pursuant to Example 2.
Figure 5:
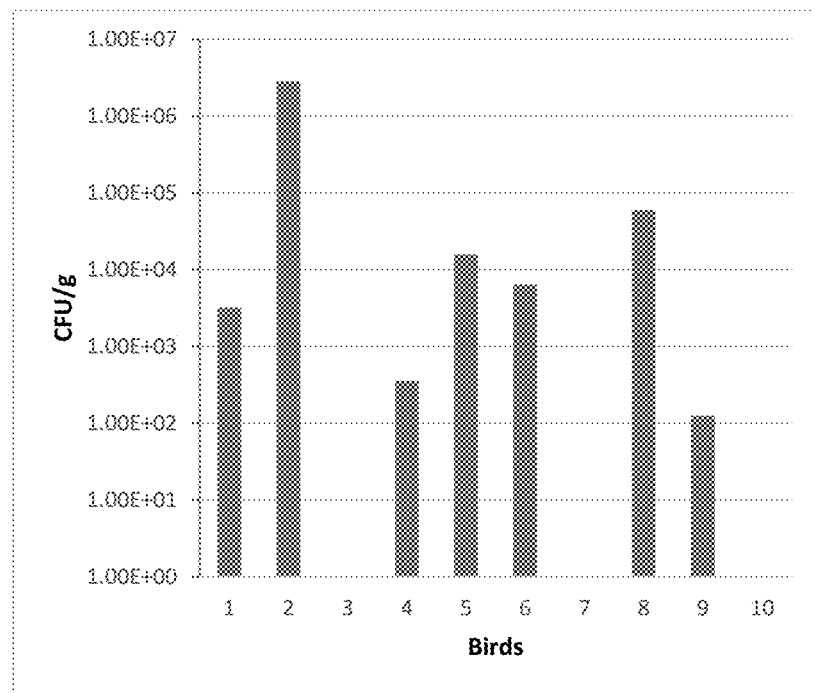
FIG. 5 is a graph showing APEC levels (CFU/g) in the GI tract of ten birds injected with ½ dose of gentamycin and treated with a composition in accordance with one embodiment of the present invention, pursuant to Example 2.
Figure 6:
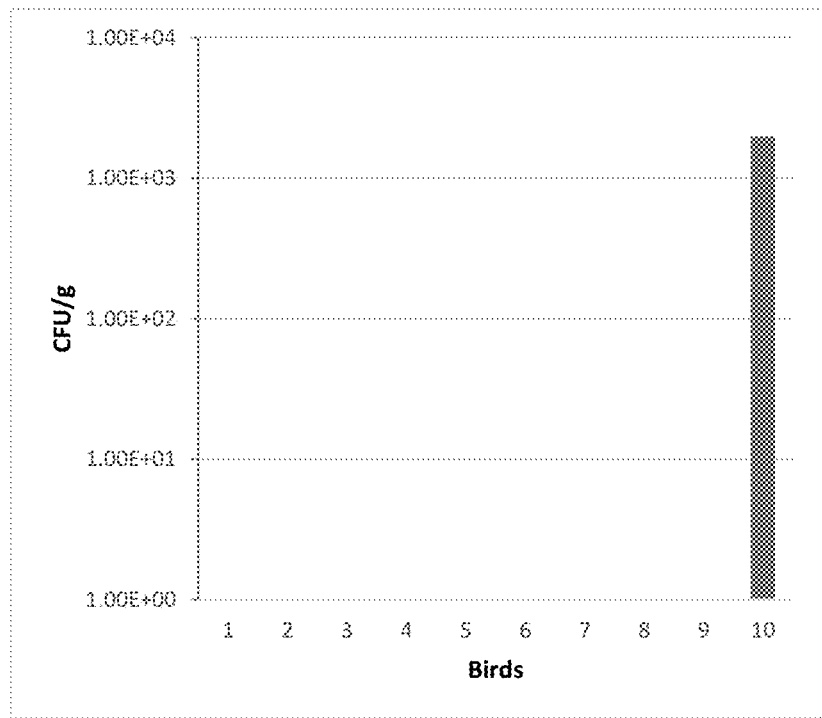
FIG. 6 shows APEC levels (CFU/g) in the GI tract of ten birds not injected with gentamycin but treated with a composition in accordance with one embodiment of the present invention, pursuant to Example 2.

The pathogen counts represented in CFU/g of tissue are shown in FIGS. 3, 4, 5 and 6. Birds that were injected with gentamycin and untreated, i.e., not treated with the product, in accordance with this embodiment of the present invention, had on average the lowest APEC level of $6.6 \times 10^1$ CFU/g and 2 out of the 10 birds sampled had detectable levels of APEC (FIG. 3). The next lowest level of APEC were birds not injected with gentamycin but treated with the product, in accordance with this embodiment of the present invention, which had an average APEC level of $1.9 \times 10^2$ CFU/g and 1 out of 10 birds with a detectable level of APEC (FIG. 6). Birds in the other treatments had statistically higher APEC levels but the results were confounded by the day-of hatch colonizing levels of APEC in these birds, which ranged from $1.5 \times 10^4$ to $7.7 \times 10^5$ CFU/g (not shown). Due to the initial high levels of APEC these treatments cannot be reliably analyzed as the high levels at the day-of hatch confound the results.

D. Discussion.

Both the gentamycin treatment only group and the group treated only with the product, in accordance with this embodiment of the present invention, were effective at controlling the APEC populations at 12-15 days after hatching. This indicates that the product, in accordance with this embodiment of the present invention, may be an effective alternative for antibiotics for establishing a healthy day-of hatch GI microbiota and controlling APEC.

Given the confounding levels of APEC in the negative control and the positive control (both treatments) in this study, only a limited amount of information is available for analysis and interpretation. However these data do indicate that given the high initial load of APEC in the GI tracts of the day-of hatch birds, even combined treatment of the gentamycin and the product, in accordance with this embodiment of the present invention, were not entirely effective at controlling the APEC population after 12-15 days.

Example 3: The Effect of Gentamycin on Avian Pathogenic *E. coli* Levels in the Gastrointestinal Tract of Young Broiler Chicks Treated with the Product in Accordance with One Embodiment of the Present Invention A. Introduction The first moments of life are crucial to a young broiler's development of a balanced and healthy microbiome (Stanley et al., 2014). Microbes from the environment make their way into the newly exposed gastrointestinal tract (GIT) of the chick and begin to occupy niches and compete for resources (Pedroso et al., 2005; Ranjitkar et al., 2016; Stanley et al., 2014). These early colonizing bacteria set the stage for immune function, bacterial homeostasis and nutritional processing for the duration of the bird's life (Danzeisen et al., 2013; Konsak et al., 2013; Stanley et al., 2012; Yin et al., 2009). All of these factors contribute to the efficiency and profitability of various poultry industries. In today's ultra-sanitized broiler production systems, newly-hatched chicks are passively inoculated by organisms from the bird's immediate environment (Stanley et al., 2014). With sterilization as the main goal, sanitation methods give little consideration to the retention or introduction of beneficial microorganisms after sanitation is complete, and as total sterilization is nearly impossible, those microbes that do persist vary in number and taxa. This means that microbial levels and compositions in the bird's GIT are often irregular and populated with undesirable organisms such as avian pathogenic *Escherichia coli* (APEC).

APEC is a causative agent for colibacillosis in birds in the form of airsacculitis, cellulitis, pericarditis, and perihepatitis (Barnes H J et al., 2008). Colibacillosis infections are of considerable concern for the poultry industry as they are the responsible for high rates of bird death and are the most reported reason for processing rejection (Georgopoulou et al., 2005). This can be achieved by reducing pathogen levels in the GIT by direct inhibition through exposure to antimicrobial compounds and by competitive exclusion of pathogens and immune modulation by probiotic microorganisms.

Conventionally, antibiotics such as in ovo injection of gentamycin have been used to control bacterial challenges such as APEC in the hatchery. However, today as poultry companies compete for the never antibiotic use (NAU), i.e., antibiotic-free, poultry market, alternatives to antibiotics used in the hatcheries are being explored. Probiotics or direct-fed microbials (DFM) are one of the more viable alternatives given the advancement of the science in recent years and acceptable costs of the products for commercial use. Accordingly, there is a recognized need for products and methods to impact the colonization of lactic acid bacteria (LAB) and reduce pathogenic bacterial populations in day-of hatch birds without the use of antibiotics. Colonizing the day-of hatch chicks with LAB can aid in developing intestinal mucosa and gut-associated lymphoid tissue critical for immunological protection (Brisbin et al., 2010, 2011; Haghighi et al., 2006). The LAB can also provide a competitive environment to exclude or reduce the APEC populations in the day-of hatch birds. Combining LAB with *Bacillus* strains capable of controlling the growth of the APEC population should result in reduced incidence of disease and improve the performance without the use of antibiotics.

The purpose of this study was to measure the microbial pathogen loads of bird treated with the product, in accordance with this embodiment of the present invention, (referred to herein as "treated"), when such birds were also treated with and without in ovo injection of gentamycin. The GITs of representative birds in each treatment group were sampled at 3 days of age and measured for APEC. Inventors' data shows that pathogen levels were not statistically different between treatment groups. It can be concluded that treatment with gentamycin in ovo does not affect the enteric APEC levels in young broiler GITs treated with the product, in accordance with this embodiment of the present invention.

B. Materials and Methods

Design: A representative group of 10 broiler chicks from 10 different hen flocks were sacrificed, and their GITs collected at 3 days of age, both with and without prior in ovo treatment of ½ dose of gentamycin, for a total of 200 GITs. All birds were treated with the product, in accordance with this embodiment of the present invention.

The product, in accordance with this embodiment of the present invention was a *Bacillus/Lactobacillus* combination product. The microbial components of which were comprised of three bacterial strains; *Bacillus* 1104 (5%), *Bacillus* 1781 (5%) and *L. salivarius* Ls-33 (90%). The product was applied at the hatchery to newly hatched chicks via a spray cabinet.

Processing gastrointestinal tracts: 10 DOH chicks from each flock were sacrificed and the GITs from the duodenal loop to the cloaca were removed and transported in sterile Whirl-pak® bags (B01297, Nasco, Fort Atkinson, Wis.) on ice. Upon arrival the ceca and lower gastrointestinal tract were removed and the remaining GIT was cut longitudinally, diluted with 99 mL of sterile 0.1% Bacto™ Peptone (Becton, Dickinson and Company, Sparks, Md.) and masticated at 300 rpm, for 1 min in a Stomacher (Model 400 circulator, Seward, England) to make a 1E-2 dilution. Serial dilutions were made and pour plated in duplicate with both CHROMagar™ ECC to enumerate *E. coli*. 50 mL of the remaining 1E-2 dilution was spun down and frozen for quantitative polymerase chain reaction (qPCR) analysis.

APEC screening: Typical *E. coli* colonies on CHROMagar™ appear blue. After 12-24 h of incubation at 37° C., all blue colonies were counted and recorded as *E. coli* CFU/g counts. Five isolated blue colonies from each bird were picked and enriched in TSB (Becton, Dickenson & Company). After enrichment genomic DNA was extracted from each isolate then APEC pathotype was determined using multiplex polymerase chain reaction (PCR). In order to be considered APEC, an *E. coli* isolate had to contain at least two of the five following APEC-associated virulence genes in its genome: hlyF, ompT, iroN, iss, iutA (Johnson et al., 2008). The reaction was run according to Johnson et al., 2008. The PCR product was then run though capillary gel electrophoresis using a Fragment Analyzer™ from Advance Analytical Technologies, Inc. and visualized on PROsize 2.0 (Advance Analytical Technologies, Inc.) APEC levels for each bird were determined by multiplying the weight-adjusted *E. coli* CFU/g counts by the percent of presumptive isolates from each bird that were confirmed to be APEC.

Counts and Statistics: Pathotype levels for each bird were determined by multiplying the weight-adjusted presumptive CFU/g counts by the percent of presumptive isolates from each bird that were revealed to be pathogenic (*C. perfringens* or APEC) and then taking the log 10 of the product. Birds that did not produce any detectable colonies on agar plates or birds that did not produce any confirmed pathogens though screening were assigned a value of 0 CFU/g. Statistical analysis for the comparison of untreated vs treated birds was run using a Mann-Whitney t-test. Significant difference threshold was set at $p<0.05$.

C. Results and Discussion

Figure 7:
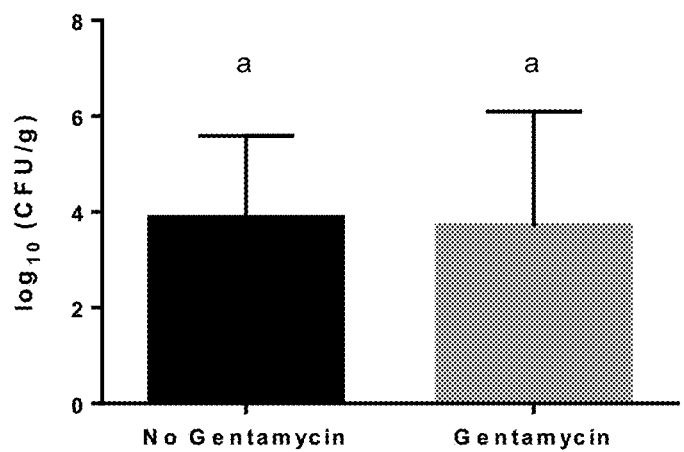
FIG. 7 is a graph showing the average levels of APEC ($\log_{10}$ CFU/g) with standard deviation in both a group treated with a composition in accordance with one embodiment of the present invention and not injected with gentamycin and a group treated with a composition in accordance with one embodiment of the present invention and injected with a ½ dose of gentamycin, pursuant to Example 3.

Avian pathogenic *E. coli* levels from each treatment group are shown in FIG. 7. APEC levels were not statistically different between gentamycin-treated and untreated birds. Inventors' data suggests that gentamycin does not provide an advantage or disadvantage when used in tandem with the product, in accordance with this embodiment of the present invention, with respect to enteric APEC levels in young broilers. These data show that the effectiveness of the *Bacillus/Lactobacillus* combination product, according to one embodiment of the present invention, to reduce avian pathogenic *E. coli* in broilers is unaffected by in ovo gentamycin treatment. This result is significant for growers who may have gentamycin incorporated into their system or for cases of therapeutic treatment with gentamycin.

Example 4: The Effect of the Lactic Acid Bacterial *Bacillus* Combination Product, According to One Embodiment of the Present Invention, for Birds at Day-of Hatch on the Microbiota and Potential Pathogens in the Intestinal Tract of One Day Old Turkeys A. Introduction Most commercial poultry production systems require that birds be transported twice over their lifetime. Once from the hatchery to the production facility and later to the processing plant. These journeys may just be for a few kilometers or they may last for hours, but all procedures involved in handling and transporting animals are very stressful for animals. Stress is known to suppress the immune system and impact gut barrier function making animals more susceptible to pathogens (Gadde et al., 2017). Transport stress to the production facility also comes at a crucial time for development of the microbiota of a young bird's gastrointestinal tract (Carver et al., 2002). The initial bacteria that colonize play a crucial role in establishing microbial populations that will affect gut health and digestion as well as developing the immune system (Cox et al., 2014). Effects that will last throughout production. In general, it is recognized that the majority of gut microbiota are vertically transmitted from the mother to the offspring with some diversity through horizontal transmission from the environment (Inoue and Ushida, 2003). In poultry the hatching chick is exposed to bacteria within the egg, on the egg surface and in the nest environment (Martin-Vivaldi et al., 2014; Ruiz-Rodriguez et al., 2014). However, in modern commercial turkey production the eggs are removed from the hen, washed and sanitized before the poults are hatched. The poults are then raised without exposure to adult birds and are therefore not exposed to the same bacteria that they would be naturally. Although there may be some maternal transmission of bacteria within the egg it is likely that the majority of the microbiota is obtained through horizontal transmission from the food, farmers and the environment (Pedroso et al., 2005). This is supported by a study which indicated that there was large variability in microbiota composition within three flocks of broilers from the same hatchery which were raised under similar conditions (Stanley et al., 2013). In effect, microbial succession can be initiated by immediately inoculating the gastrointestinal tract of birds as they hatch with beneficial lactic acid bacteria (LAB) (Ballou et al., 2016). These LABs were chosen because they are colonizers of the intestinal tract which are known to competitively exclude potential pathogens and aid in developing gut-associated lymphoid tissue. At the same time adding *Bacillus* species that produce bacteriocins inhibitory to avian pathogenic *Escherichia coli* (APEC) will reduce levels of these pathogens that are prevalent in the environments the birds are exposed to and can increase during times of stress (Tagg et al., 1976). This study was done to determine whether the combination of lactic acid bacteria and bacilli would prevent early establishment of potential pathogens and improve the diversity of the microbiota in the gastrointestinal tract of one day old poults after transport stress.

B. Materials and Methods.

Forty day old poults were harvested after traveling from a hatchery in Missouri to a commercial turkey producer in Utah, a distance of over a thousand miles. Twenty of the birds were collected prior to the hatchery treating poults with a direct fed microbial (DFM) product comprising, according to this embodiment of the present invention, *Bacillus* strains 1104 (5%) and 1781 (5%), *L. salivarius* Ls-33 (45%) and *L. plantarum* Lp-115 (45%) Twenty of the birds were collected after the hatchery had treated the birds with the product (referred to herein as "treated"). The entire gastrointestinal tract was placed on ice and transported overnight on ice to inventors' facility for processing. Upon arrival at the laboratory the entire gastrointestinal tract from duodenal loop to ileal-cecal junction was cut longitudinally and placed in a sterile, filtered Whirl-pak® bag (B01348, Nasco, Fort Atkinson, Wis.). 99 mL of sterile 0.1% Bacto™ Peptone (Becton, Dickinson and Company, Sparks, Md.) was added to the bag then the sections were masticated at 300 rpm, for 1 min in a Stomacher (Model 400 circulator, Seward, England). Serial dilutions were made and pour plated in duplicate with CHROMagar™ ECC to enumerate *E. coli*.

Typical *E. coli* colonies on CHROMagar™ appear blue. After 12-24 h of incubation at 37° C., all blue colonies were counted and recorded as presumptive APEC CFU/g counts. Five isolated blue colonies from each bird were picked and enriched in TSB (Becton, Dickenson & Company). Genomic DNA was extracted from each isolate using the following gDNA extraction method: Add 20 µL of lysozyme (100 mg/mL) to 500 µL of overnight growth in TSB and incubate at 37° C. for 30 min, add 300 µL of lysis buffer (6 M Guanidine, 20% Triton-X 100, 10 mM Tris-HCl, pH 7.5) and incubate at 25° C. for 15 min, add 20 µl of Protease K (NEB, 800 U/ml) and incubate at 55° for 30 min, transfer 400 µL of lysate to a Wizard® SV 96 Binding Plate from Promega and continue with manufacturer's filtration instructions from Promega Wizard® SV 96 Genomic DNA Purification System starting from step 3.C.4 (April 2015 revision).

APEC pathotype was determined using multiplex polymerase chain reaction (PCR). In order to be considered APEC, an *E. coli* isolate had to contain at least two of the five following APEC-associated virulence genes in its genome: hlyF, ompT, iroN, iss, iutA (Johnson et al., 2008). Each reaction mixture contained 4 mM magnesium chloride (Invitrogen), 0.25 mM deoxynucleoside triphosphates (Invitrogen), 0.25 µM each primer (Eurofins), and 1 U Platinum® Taq DNA Polymerase (Invitrogen) and 5 µL of template gDNA. The reaction was run on an Applied Biosystems Veriti® Thermal Cycler with the following protocol: 94° C. for 2 min; 25 cycles of 94° C. for 30 s, 63° C. for 30 s, 68° C. for 3 min; and a final cycle of 72° C. for 10 min. The PCR product was then run though capillary gel electrophoresis using a Fragment Analyzer™ from Advance Analytical Technologies, Inc. and visualized on PROsize 2.0 (Advance Analytical Technologies, Inc).

Counts and Statistics: Pathotype levels for each bird were determined by multiplying the weight-adjusted presumptive CFU/g counts by the percent of presumptive isolates from each bird that were revealed to be pathogenic (APEC) and then taking the log 10 of the product. Birds that did not produce any detectable colonies on agar plates or birds that did not produce any confirmed pathogens though screening were assigned a value of 500 CFU/g for APEC.

Statistical analysis for the comparison of untreated vs treated birds was run using a Mann-Whitney t-test. Significant difference threshold was set at $p<0.05$.

Microbial cell pellets were collected by centrifugation for 10 min at 3500× g from 20 ml of the first dilution of the masticated intestinal tracts. Bacterial genomic DNA was isolated from the pellets using the DNeasy PowerSoil Kit (#12888-100, MO BIO Laboratories, a QIAGEN company, Carlsbad, Calif.). DNA was extracted per the manufacturer's protocol with the one modification being that samples were homogenized for 2 min in the Mini-BeadBeater-16 (Biospec Products, Inc., Bartlesville, Okla.).

Terminal Restriction Fragment Length Polymorphism (T-RFLP) of the total bacterial community was performed by amplifying the bacterial 16S rDNA gene with 6-carboxyfluorescein labeled 27F-YM-(AGAGTTT-GATYMTGGCTCAG; SEQ ID NO: 1) and unlabeled 785R (ACTACCRGGGTATCTAATCC; SEQ ID NO: 2) primers. Each reaction contained 10 µl 10×PCR buffer, 3 µl 50 mM MgCl2, 2 µl 10 mM dNTPs, 10 pmol 27F-YM, 10 pmol 785R, 0.4 µl Invitrogen Platinum® Taq polymerase, 5 µl gDNA and 77.6 µl sterile ddH2O for a final volume of 100 µl/reaction. PCR amplifications were performed as follows: initial denaturation at 95° C. for 4 min; 30 cycles of denaturation at 95° C. for 30 s, annealing at 55° C. for 30 s, and elongation at 72° C. for 45 s; with a final elongation step of 72° C. for 7 min. PCR amplicons were PCR purified with the Zymo Research ZR-96 DNA Clean-up Kit and concentrated to 50 µl. Restriction digests were set up by for the enzymes MspI, BstUI and HaeIII by combining 15 µl purified PCR product, 1× reaction buffer, and 2 units of the selected restriction enzyme in a 30 µl reaction and incubated/deactivated following the manufacturer's instructions for each enzyme.

T-RFLP of the lactic acid bacterial (LAB) community was performed by amplifying the 16S rDNA gene using 6-carboxyfluorescein labeled NLAB2F (GGCGGCGTGCCTAATACATGCAAGT; SEQ ID NO: 3) and unlabeled WLAB1R (TCGCTTTACGCC-CAATAAATCCGGA; SEQ ID NO: 4) LAB specific primers (Bokulich and Mills, 2012). Each reaction contained 10 µl 10×PCR buffer, 3 µl 50 mM MgCl2, 2 µl 10 mM dNTPs, 10 pmol NLAB2F, 10 pmol WLAB1R, 0.4 µl Invitrogen Platinum® Taq polymerase, 5 µl gDNA and 77.6 µl sterile ddH$_2$O for a final volume of 100 µl/reaction. PCR amplifications were performed as follows: initial denaturation at 95° C. for 4 min; 30 cycles of denaturation at 95° C. for 30 s, annealing at 66° C. for 30 s, and elongation at 72° C. for 45 s; with a final elongation step of 72° C. for 7 min. PCR amplicons were PCR purified with the Zymo Research ZR-96 DNA Clean-up Kit and concentrated to 50 µl. Restriction digests were set up by for the enzymes MseI, Hpy188I and Hpy188III by combining 15 µl purified PCR product, 1× reaction buffer, and 2 units of the selected restriction enzyme in a 30 µl reaction and incubated/deactivated following the manufacturer's instructions for each enzyme.

The digested amplicons for both the bacteria and the LAB PCR was submitted to the High-Throughput Sequencing and Genotyping Unit of the Roy J. Carver Biotechnology Center at the University of Illinois for fragment analysis. T-RFLP profiles were normalized using Genemapper 5.0 software. Presumptive identification of peaks was made using the Microbial Community Analysis III (MiCA3) database (see, the website at mica.ibest/uidaho.edu/) and statistical analysis of peak was done by multivariate analysis of variance (MANOVA) in Applied Math's Bionumerics.

C. Results

Figure 8:
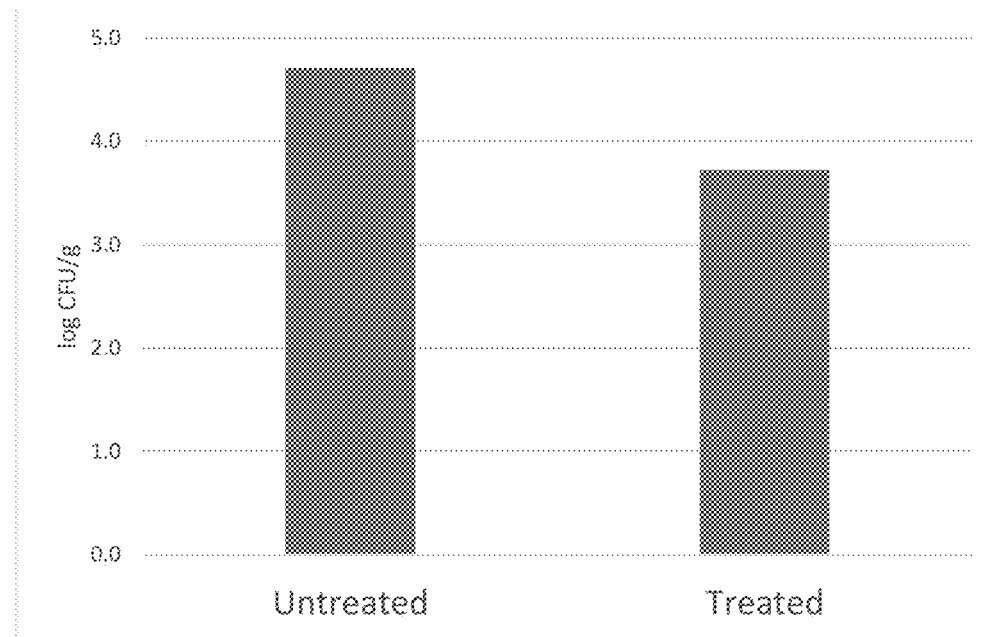
FIG. 8 is a graph showing average APEC levels ($\log_{10}$ CFU/g) in the intestine of one-day-old turkey poults in both an untreated group and a group treated with a composition in accordance with one embodiment of the present invention, pursuant to Example 4.
Figure 9:
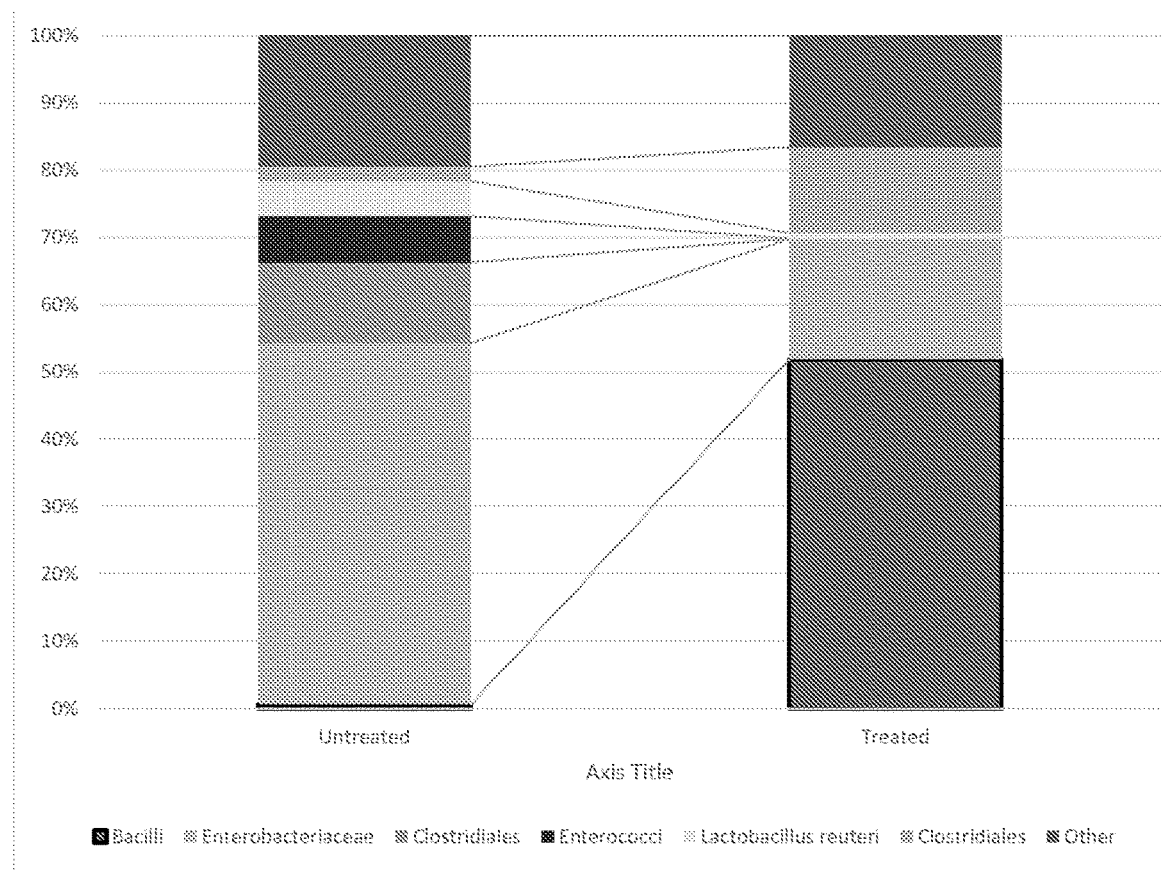
FIG. 9 is a graph showing the proportions of each bacterial peak labeled with their presumptive MICA identification that were significantly different by MANOVA analysis between the untreated group of one-day-old turkey poults and the group of one-day-old turkey poults treated with a composition in accordance with one embodiment of the present invention, where the bacterial peaks representing the bacteria in a composition in accordance with one embodiment of the present invention are outlined and where minor peaks and peaks that were not significantly different are grouped together as "Other," pursuant to Example 4.

The average APEC levels of day old treated poults (those treated with the direct fed microbial product, according to this embodiment of the present invention), were significantly lower at 3.7 log CFU/g than the untreated poults at 4.7 log CFU/g (FIG. 8). The bacterial communities of the intestinal tract were significantly different between the treated poults and those untreated poults harvested before the direct fed microbial product was implemented at the hatchery (FIG. 9). Enterobacteriaceae, which includes *E. coli*, were predominant in the untreated birds, whereas bacilli (a component of the direct fed microbial product, according to this embodiment of the present invention) were the predominant bacteria in the treated birds. Enterococci were at significantly lower levels in the treated birds. *Lactobacillus reuteri* were higher in the untreated poults. Clostridiales populations also differed between the two groups.

Figure 10:
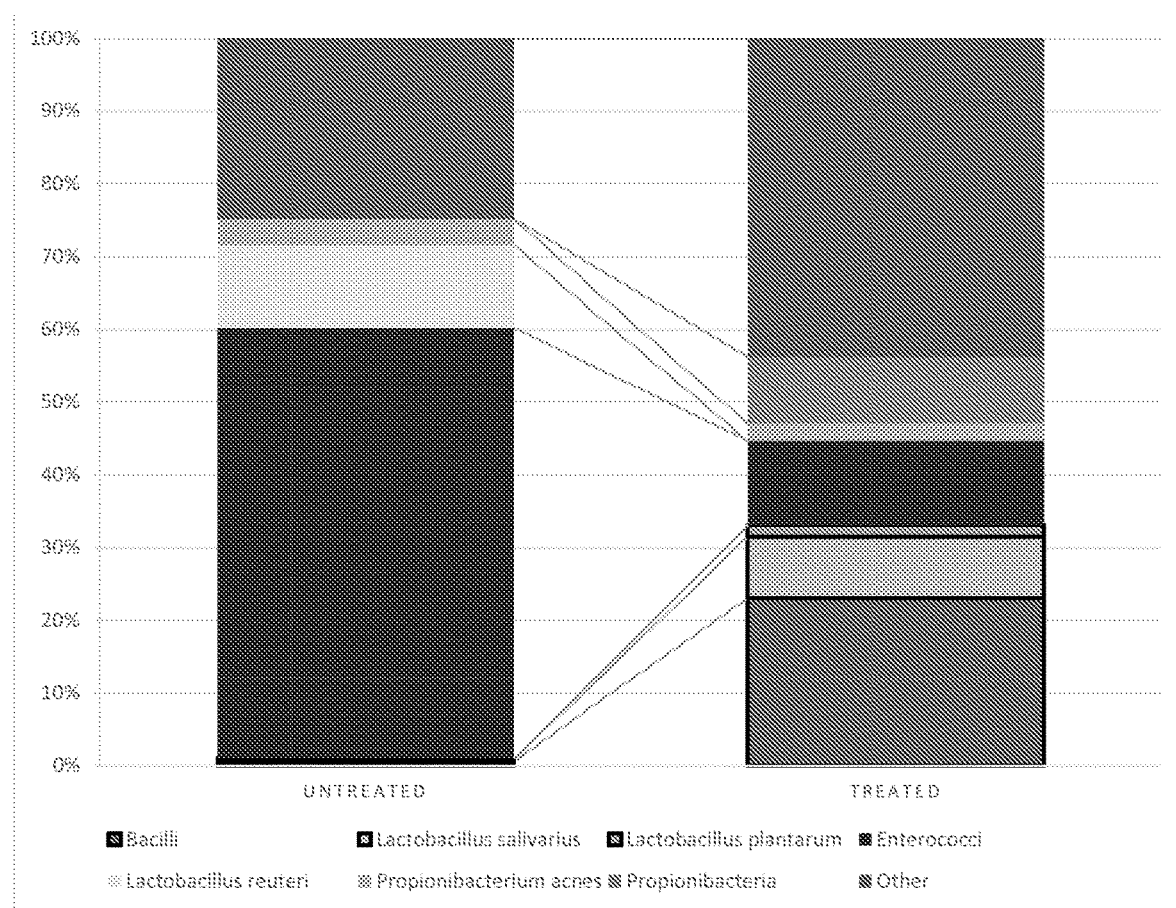
FIG. 10 is a graph showing the proportions of each lactic acid bacterial peak labeled with their presumptive MICA identification that were significantly different by MANOVA analysis between the untreated group of one-day-old turkey poults and the group of one-day-old turkey poults treated with a composition in accordance with one embodiment of the present invention, where the bacterial peaks representing the bacteria in a composition in accordance with one embodiment of the present invention are outlined, and minor peaks and peaks that were not significantly different are grouped together as "Other," pursuant to Example 4.
Figure 11:
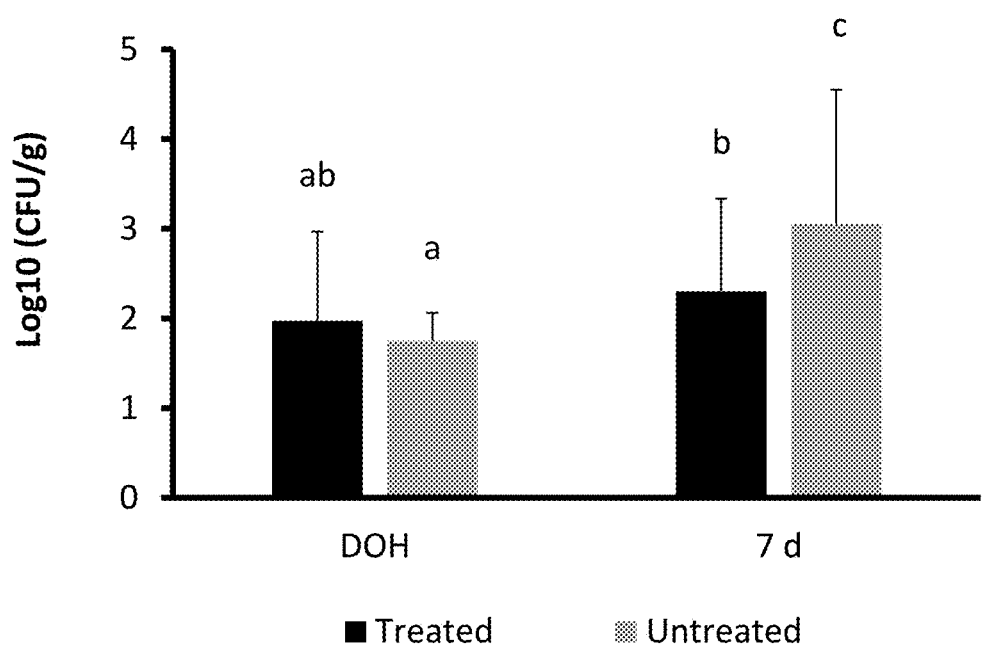
FIG. 11 is a graph showing the average APEC levels ($\log_{10}$ CFU/g) in the gastrointestinal day-of hatch (DOH) birds and 7 day old birds with standard deviation in both an untreated group and a group treated with a composition in accordance with one embodiment of the present invention, pursuant to Example 5.

A more detailed analysis of the LAB communities indicated the predominant LAB were enterococci in the untreated poults and again bacilli (a component of the direct fed microbial product, according to this embodiment of the present invention), were predominant in the treated poults (FIG. 10). The LAB *L. salivarius* and *L. plantarum*, (also component of the direct fed microbial product, according to this embodiment of the present invention) were significantly higher in the intestinal tract of the treated birds. Also, *L. reuteri* were higher in the untreated poults as indicated in the bacterial communities. Types of propionibacteria differed between the two groups with *P. acnes* higher in the untreated birds and other propionibacteria in the treated birds.

D. Discussion

The direct fed microbial product, according to this embodiment of the present invention, significantly reduced levels of pathogenic *E. coli* by one log in the gastrointestinal tract of poults. The reduction of pathogenic *E. coli* was confirmed with bacterial community data as Enterobacteriaceae proportions, which includes pathogenic *E. coli*, were lower in treated poults. The bacilli, forming a component of the direct fed microbial product, were responsible for displacing the Enterobacteriaceae, as bacilli were the predominant bacteria one day after the poults were fed the DFM at the hatchery. Other bacterial changes included lower proportions of enterococci and *L. reuteri* in treated poults as well as differing clostridial populations between the two groups. A detailed analysis of the LAB bacteria indicated that the bacteria comprising the direct fed microbial product, according to this embodiment of the present invention, displaced the enterococci in untreated poults at day one. In conclusion, therefore, the bacteria comprising the direct fed microbial product, according to this embodiment of the present invention, displaced pathogenic *E. coli* and enterococci in the gastrointestinal tract of treated poults resulting in lower levels of potential pathogens and improved bacterial diversity.

Example 5: The Effect of the Product in Accordance with One Embodiment of the Present Invention, on Avian Pathogenic *E. coli* and *Clostridium perfringens* Levels in the Gastrointestinal Tract of Young Broiler Chicks and Performance of Commercial Broiler Flocks A. Introduction The first moments of life are crucial to a young broiler's development of a balanced and healthy microbiome (Stanley et al., 2014). Microbes from the environment make their way into the newly exposed gastrointestinal tract (GIT) of the chick and begin to occupy niches and compete for resources (Pedroso et al., 2005; Ranjitkar et al., 2016; Stanley et al., 2014). These early colonizing bacteria set the stage for immune function, bacterial homeostasis and nutritional processing for the duration of the bird's life (Danzeisen et al., 2013; Konsak et al., 2013; Stanley et al., 2012; Yin et al., 2009). All of these factors contribute to the efficiency and profitability of various poultry industries. In today's ultra-sanitized broiler production systems, newly-hatched chicks are passively inoculated by organisms from the bird's immediate environment (Stanley et al., 2014). With sterilization as the main goal, sanitation methods give little consideration to the retention or introduction of beneficial microorganisms after sanitation is complete, and as total sterilization is nearly impossible, those microbes that do persist vary in number and taxa. This means that microbial levels and compositions in the bird's GIT are often irregular and populated with undesirable organisms such as avian pathogenic *Escherichia coli* (APEC) and *Clostridium perfringens*.

Irregularities in the commercial broiler industry are highly problematic. A jeopardized microbial composition in the gastrointestinal tract may negatively impact weight uniformity, bird mortality, and disease instances, all of which decrease profitability for the grower. A healthy and uniform gut microbiome can be achieved in part by reducing pathogen levels in the GIT by direct inhibition through exposure to antimicrobial compounds (Rolfe, 2000) and by competitive exclusion of pathogens (Kerr et al., 2013) and immune modulation by probiotic microorganisms (Havenaar and Spanhaak, 1994).

As for this embodiment, the product, according to one aspect of the invention, is a gel-based direct fed microbial, applied in a hatchery, designed to deliver two pathogen-inhibiting *Bacillus* strains and an immune-strengthening *Lactobacillus salivarius* strain and *Lactobacillus plantarum* strain to freshly hatched chicks. Members of the genus *Bacillus* are known to produce a diverse and strain-specific array of antimicrobial compounds known as bacteriocins (Tagg et al., 1976). The inventors have screened and isolated two strains of *Bacillus* that show a strong inhibitory effect on APEC and *C. perfringens*. These strains comprise 10% of the microbial components of the product, according to this embodiment of the present invention. The remaining 90% of the microbial formulation is comprised of Ls-33 and Lp-115, strains of *Lactobacillus* which exhibit various beneficial immune modulation functions.

An in vivo study was designed to measure the effect of the product, according to this embodiment of the present invention, on flock performance. A southeastern US broiler hatchery treated flocks with the product, according to this embodiment of the present invention (referred to herein as "treated"), in alternating weeks over a 12 week period. Birds were monitored for performance metrics throughout the duration of their lives. GITs of day-of hatch and week old birds that were both treated and untreated with the product, according to this embodiment of the present invention, were sampled for APEC and *C. perfringens* type A levels.

B. Materials and Methods

Design: A southeastern US broiler hatchery, with a placement rate of 1 million birds per week, collaborated for this study. Chicks were treated with the product, according to one embodiment of the present invention, in alternating weeks over a 12-week period with the other weeks used as untreated controls. Gastrointestinal tracts (GIT) from a sub set of treated and untreated birds were collected from day-of hatch chicks at the hatchery and week old broiler chicks from the same flocks after placement. For each week of sampling, 10 GITs from chicks at both ages from three breeder flocks were collected for a total of 240 GIT samples tested in this trial.

The product, in accordance with this embodiment of the present invention was a *Bacillus/Lactobacillus* combination product. The microbial components of which were comprised four bacterial strains; *Bacillus* 1104 (5%), *Bacillus* 1781 (5%), *Lactobacillus salivarius* Ls-33 (45%) and *Lactobacillus plantarum* Lp-115 (45%).

Processing of Gastrointestinal Tracts: Selected broilers were sacrificed and the gastrointestinal tracts from the duodenal loop to the cloaca were removed and transported in sterile Whirl-pak® bags (B01297, Nasco, Fort Atkinson, Wis.) on ice. Upon arrival, the entire tract, from duodenum to the ileocecal junction were rinsed with ~5 mL sterile 0.1% Bacto™ Peptone (Becton, Dickinson and Company, Sparks, Md.) broth (day-of hatch chicks were not rinsed), cut longitudinally, and placed in a sterile, filtered Whirl-pak® bag (B01348, Nasco, Fort Atkinson, Wis.). 99 mL of sterile 0.1% peptone was added to the bag then the sample was masticated at 300 rpm, for 1 min in a Stomacher (Model 400 circulator, Seward, England). Serial dilutions were made and pour plated in duplicate with both CHROMagar™ ECC to enumerate *E. coli*, and *perfringens* TSC agar base (Oxoid™) with D-cycloserine (Sigma, 400 mg/L) for *Clostridium* spp. enumeration.

APEC Screening: Typical *E. coli* colonies on CHROMagar™ appear blue. After 12-24 h of incubation at 37° C., all blue colonies were counted and recorded as presumptive APEC CFU/g counts. Five isolated blue colonies from each bird were picked and enriched in TSB (Becton, Dickenson & Company) if possible. Genomic DNA was extracted from each isolate using the following gDNA extraction method: Add 20 µL of lysozyme (100 mg/mL) to 500 µL of overnight growth in TSB and incubate at 37° C. for 30 min, add 300 µL of lysis buffer (6 M Guanidine, 20% Triton-X 100, 10 mM Tris-HCl, pH 7.5) and incubate at 25° C. for 15 min, add 20 µl of Protease K (NEB, 800 U/ml) and incubate at 55° for 30 min, transfer 400 µL of lysate to a Wizard® SV 96 Binding Plate from Promega and continue with manufacturer's filtration instructions from Promega Wizard® SV 96 Genomic DNA Purification System starting from step 3.C.4 (April 2015 revision).

APEC pathotype was determined using multiplex polymerase chain reaction (PCR). In order to be considered APEC, an *E. coli* isolate had to contain at least two of the five following APEC-associated virulence genes in its genome: hlyF, ompT, iroN, iss, iutA (Johnson et al., 2008). Each reaction mixture contained 4 mM magnesium chloride (Invitrogen), 0.25 mM deoxynucleoside triphosphates (Invitrogen), 0.25 µM each primer (Eurofins), and 1 U Paltinum® Taq DNA Polymerase (Invitrogen) and 5 µL of template gDNA (Johnson et al., 2008). The reaction was run on an Applied Biosystems Veriti® Thermal Cycler with the following protocol: 94° C. for 2 min; 25 cycles of 94° C. for 30 s, 63° C. for 30 s, 68° C. for 3 min; and a final cycle of 72° C. for 10 min. The PCR product was then run though capillary gel electrophoresis using a Fragment Analyzer™ from Advance Analytical Technologies, Inc. and visualized on PROsize 2.0 (Advance Analytical Technologies, Inc.).

*C. perfringens* Type A Screening: Presumptive *C. perfringens* isolates appear black on *perfringens* TSC agar base. All black colonies were counted and recorded as presumptive *C. perfringens* CFU/g counts. Five isolated black colonies from each bird were picked and grown in RCM broth (Oxoid™) if possible. Genomic DNA was extracted from each isolate using the Roche Applied Science High Pure PCR Template Kit.

*C. perfringens* toxinotype was determined using polymerase chain reaction (PCR) to amplify the alpha toxin gene. In order for an isolate to be considered *C. perfringens* Type A it had to contain the alpha toxin gene, otherwise it was categorized as a non-*perfringens Clostridium* species. Each reaction mixture contained 2.5 μL 10×PCR buffer (Invitrogen), 1.6 μL magnesium chloride (Invitrogen), 0.5 μL deoxynucleoside triphosphates (Invitrogen), 100 pmol primers (Eurofins), and 1 U Paltinum® Taq DNA Polymerase (Invitrogen) and 2 μL of template gDNA, 7.8 μL of ddH20 (Yoo et al., 1997). The reaction was run on an Applied Biosystems Veriti® Thermal Cycler with the following protocol: 5 min at 94° C., followed by 30 incubation cycles consisting of 1 min at 55° C., 1 min at 72° C., and 1 min at 94° C. The PCR product was then run though capillary gel electrophoresis using a Fragment Analyzer™ from Advance Analytical Technologies, Inc. and visualized on PROsize 2.0 (Advance Analytical Technologies, Inc.).

Performance: Performance metrics of the flocks tested above were monitored over the entire growing period, from flock placement to processing. Performance data was collected and generated by the collaborating commercial broiler company. Data-gathering protocols and statistical methods used by the collaborator were not made available for this study. All performance data in this study was submitted to us in the fashion that it is presented here, unless otherwise stated.

Counts and Statistics: Pathotype levels for each bird were determined by multiplying the weight-adjusted presumptive CFU/g counts by the percent of presumptive isolates from each bird that were revealed to be pathogenic (*C. perfringens* or APEC) and then taking the log 10 of the product. Birds that did not produce any detectable colonies on agar plates or birds that did not produce any confirmed pathogens though screening were assigned a value of 50 CFU/g for APEC and 0 CFU/g for *Clostridium perfringens*. Statistical analysis for the comparison of untreated vs treated birds was run using a Mann-Whitney t-test on the log 10 transformed counts. Significant difference threshold was set at $P<0.05$.

C. Results

The average APEC levels by age and treatment group are represented in CFU/g or tissue are shown in FIG. 11. Day-of hatch chicks were not statistically different between treatment groups, but 7 day old untreated birds harbored an average APEC level of $1.1\times10^3$ CFU/g, which was significantly higher than the 2.0×102 CFU/g APEC level in the 7 day old treated birds. *C. perfringens* levels were below detectable limits in all GITs of both ages and treatment groups.

Performance data is shown in Table 1. Treated birds had improved 7-day mortality and coefficient of variation (CV). There was no significant difference in the 7-day mortalities, however, the improvement in the CV of weight was statistically significant.

D. Discussion

These data provide strong evidence that product, in accordance with one embodiment of the present invention, lowers APEC levels in the GIT. As shown in FIG. 11, APEC levels in treated GITs remained unchanged whereas APEC levels in untreated birds increased more than a log. Reduction of these pathogens can diminish cases of disease in broilers such as colibacillosis and necrotic enteritis, diseases which present significant financial liability to the poultry industry. This is supported by performance data that indicated a numerical improvement in 7-day mortality and statistical improvement in the coefficient of variation for weight. The inventors' research shows that including the product, in accordance with this embodiment of the present invention, is effective in reducing APEC prevalence in young broilers and improving the coefficient of variation of weight therefore decreasing the disease-burden in commercial broiler operations and improving uniformity of the bird.

Table 1. Averaged commercial performance data from the broiler flocks throughout the entire growth period. Data shown here is the mean of 6 weeks of production representing over 1 million birds per week. 7-day mortality was is not statistically significant by Mann-Whitney t-test ($P<0.05$).

TABLE 1

| Treatment | 7-day mortality (%) | Livability (%) | Age (days) | Weight (lbs) | Average daily weight gain (lbs) | Feed conversion ratio | Coefficient of variability weekly* |
|---|---|---|---|---|---|---|---|
| Treated | 1.59 | 96.45 | 34.08 | 3.82 | 0.112 | 1.65 | 10.18 |
| Untreated | 1.64 | 96.57 | 33.81 | 3.85 | 0.1145 | 1.63 | 10.65 |

Differences considered statistically significant (*p = 0.05)

Example 6: Anti-Inflammatory Effects of *Lactobacillus salivarius* and *L. plantarum* in an Intestinal Epithelial Cell Line A. Introduction Many lactic acid bacteria are known to confer gastrointestinal health benefits when present as part of the commensal microbiota or when ingested as a probiotic (Jin et al., 1998). *Lactobacillus* spp. have been identified as critical early colonizing bacteria in many organisms, including avian species, and this initial colonization of beneficial bacteria in the gastrointestinal tract in the young animal has been deemed essential throughout its life. Early establishment of lactic acid bacteria (LAB), including *Lactobacillus* spp., plays a vital role in stabilizing intestinal homeostasis, Quantitative real-time PCR was performed to determine gene expression of the IEC-6 cells using primer sets displayed in Table 2, and β-actin was used as a reference gene. Data are expressed as fold change in gene expression relative to unstimulated control cells.

TABLE 2

Rat specific primer sets used in quantitative real-time PCR.

| Gene Primer | Primer Sequence Forward | Primer Sequence Reverse | PCR Product (bp) |
|---|---|---|---|
| β-Actin | 5'-TGACGAGGCCCAGAGCAAGA-3' SEQ ID NO: 5 | 5'-ATGGGCACAGTGTGGGTGAC-3' SEQ ID NO: 6 | 331 |
| MIP2 | 5'-CCCCTTGGTTCAGAGGATCG-3' SEQ ID NO: 7 | 5'-TTGATTCTGCCCGTTGAGGT-3' SEQ ID NO: 8 | 103 |
| TNF-α | 5'-GGCCCGAGGCAACACAT-3' SEQ ID NO: 9 | 5'-GGGCCATGGAACTGATGAGA-3' SEQ ID NO: 10 | 263 |
| IL-1β | 5'-CCACTGCCTTCCCTACTTCA-3' SEQ ID NO: 11 | 5'-CAGAATTGCCATTGCACAAC-3' SEQ ID NO: 12 | 159 | digestion and nutrient absorption, and nurturing mucosal conditions for immunological protection (Brisbin et al., 2010, 2011; Haghighi et al., 2006). Colonizing the gastrointestinal tract of day-of hatch chicks with lactic acid bacteria that can aid in developing intestinal mucosa and gut-associated lymphoid tissue critical for immunological protection and establishing immune homeostasis. The following study demonstrates the immunomodulatory effect of two *Lactobacillus* strains in an intestinal epithelial cell line and their ability to alleviate the inflammatory response elicited by an in vitro *Escherichia coli* lipopolysaccharide (LPS) challenge.

B. Materials and Methods.

The rat intestinal epithelial cell line IEC-6 was used to determine the inflammatory response to LPS, two *Lactobacillus* strains, and their interactive effects. Lipopolysaccharide was selected as the inflammatory challenge agent to simulate a gram negative bacterial infection. *Lactobacillus* strains (*Lactobacillus salivarius* Ls-33 and *Lactobacillus plantarum* Lp-115) were screened in a cell culture assay to determine changes in inflammatory cytokine gene expression responses with and without LPS challenge.

The IEC-6 cells were grown to confluence and plated in a 24-well tissue culture plate at 3×105 cells/well with Dulbecco's Modified Eagle's Medium (DMEM) containing 10% fetal bovine serum and 1% antibiotic (Penicillin/Streptomycin). Once the plates were confluent, the cells were washed twice with phosphate buffered saline (PBS), treatments were administered in antibiotic free media, and then incubated for 1 hr at 37° C. The following treatments were administered to respective wells containing IEC-6 cell monolayers: 1) alone (unstimulated); 2) with LPS; 3) with each *Lactobacillus* strain; and 4) with each *Lactobacillus* strain+LPS. After incubation, the cells were washed twice with PBS and incubated with 400 uL Trizol for 5 minutes. Samples were then removed from plates and placed in 1.5 mL microcentrifuge tubes, snap frozen in liquid nitrogen, and stored at −80° C. until RNA isolation. RNA extraction was performed using Direct-zol RNA Kit (Zymo Research, Irvine, Calif.) and cDNA was synthesized using the Quantinova Reverse Transcriptase kit (Qiagen, Inc., Valencia, Calif.) immediately following RNA isolation.

C. Results

Figure 12:
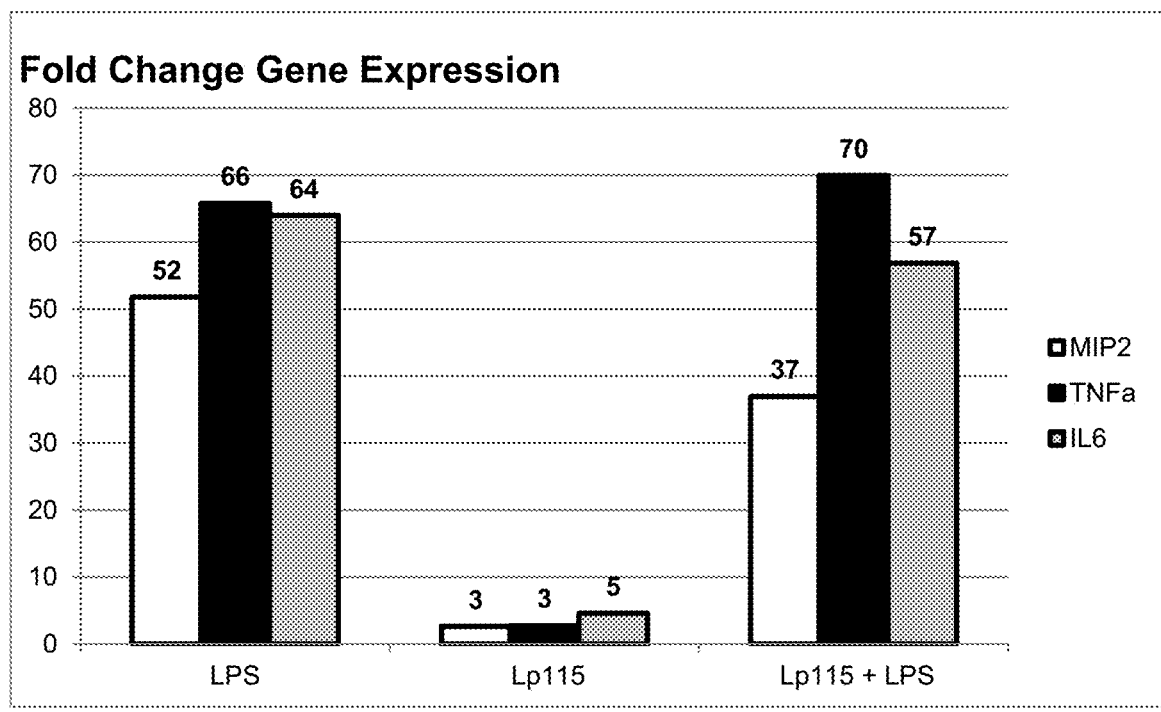
FIG. 12 is a graph showing a fold change in gene expression of the inflammatory cytokines, Macrophage Inflammatory Protein-2 (MIP2), Tumor Necrosis Factor-α (TNFα), and Interleukin-6 (IL-6) relative to unstimulated IEC-6 rat intestinal epithelial cells in response to lipopolysaccharide (LPS) and *Lactobacillus plantarum* Lp-115, pursuant to Example 6.
Figure 13:
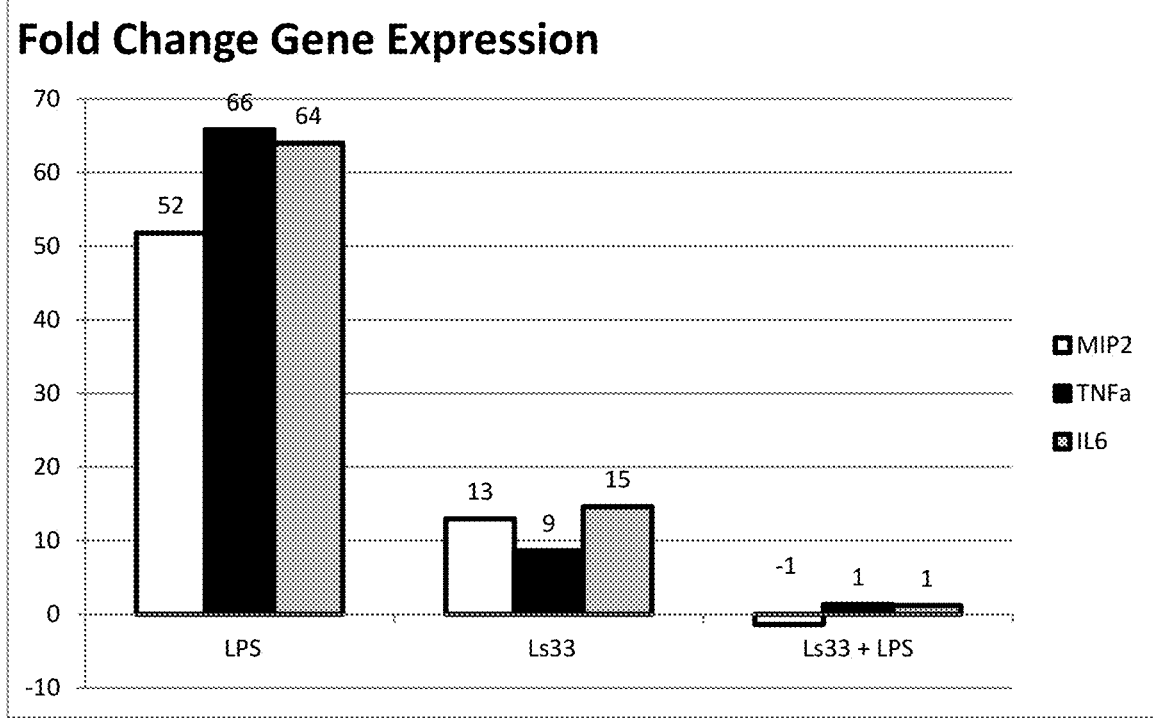
FIG. 13 is a graph showing a fold change in gene expression of the inflammatory cytokines, Macrophage Inflammatory Protein-2 (MIP2), Tumor Necrosis Factor-α (TNFα), and Interleukin-6 (IL-6) relative to unstimulated IEC-6 rat intestinal epithelial cells in response to lipopolysaccharide (LPS) and *Lactobacillus salivarius* Ls-33, pursuant to Example 6.

Lipopolysaccharide challenge in the IEC-6 rat intestinal epithelial cell line resulted in a >50-fold increase in gene expression of all three inflammatory cytokines [Macrophage Inflammatory Protein-2 (MIP2), Tumor Necrosis Factor-α (TNFa), and Interleukin-6 (IL-6)] relative to unstimulated control cells (FIG. 12 and FIG. 13). Both *L. plantarum* Lp-115 (FIG. 12) and *L. salivarius* Ls-33 (FIG. 13) resulted in a slight increase in gene expression of the three inflammatory cytokines measured, indicating these lactic acid bacteria have the ability to modulate immune responses within the intestinal epithelia. When *L. plantarum* Lp-115 was administered to the IEC-6 cell line with LPS, a similar fold increase in inflammatory cytokine gene expression was observed as when LPS was administered alone; however, when *L. salivarius* Ls-33 was administered to the IEC-6 cell line with LPS, the increase in inflammatory cytokine gene expression observed in response to LPS was completely ameliorated.

D. Discussion.

These data demonstrate the efficacy of *Lactobacillus* strains for modulating the immune response in the gastrointestinal epithelia and alleviating inflammatory responses in intestinal epithelial cells. Furthermore, *L. salivarius* Ls-33 was able to completely remedy the inflammatory response associated with LPS administration, indicating that some *Lactobacillus* strains have the ability to ameliorate the inflammation associated with a gram negative bacterial challenge in the gastrointestinal tract. Collectively, the results of this study support the use of *Lactobacillus* strains as a probiotic administered to support efficient production and improved health in and poultry.

Other embodiments and uses of the invention will be apparent to those skilled in the art from consideration from the specification and practice of the invention disclosed herein. All references cited herein for any reason, including all journal citations and U.S./foreign patents and patent applications, are specifically and entirely incorporated herein by reference. It is understood that the invention is not confined to the specific reagents, formulations, reaction conditions, etc., herein illustrated and described, but embraces such modified forms thereof as come within the scope of the following claims.

BIBLIOGRAPHY

Ballou, A. L., Ali, R. A., Mendoza, M. A., Ellis, J. C., Hassan, H. M., Croom, W. J., and Koci, M. D. (2016). Development of the chick microbiome: How early exposure influences future microbial diversity. Front. Vet. Sci. 3, 2.

Barnes H J, Nolan L, and Vaillancourt J-P (2008). Colibacillosis. In Diseases of Poultry, Saif Y M, Fadly A A, Glisson J R, McDougald L R, Nolan L, and Swayne D E, eds. (Ames, Iowa: ISU Press), pp. 691-732.

Bar-Shira, E., and Friedman, A. (2006). Development and adaptations of innate immunity in the gastrointestinal tract of the newly hatched chick. Dev. Comp. Immunol. 30, 930-941.

Bokulich, N. A., and Mills, D. A. (2012). Differentiation of mixed lactic acid bacteria communities in beverage fermentations using targeted terminal restriction fragment length polymorphism. Food Microbiol. 31, 126-132.

Brisbin, J. T., Gong, J., Parvizi, P., and Sharif, S. (2010). Effects of lactobacilli on cytokine expression by chicken spleen and cecal tonsil cells. Clin. Vaccine Immunol. CVI 17, 1337-1343.

Brisbin, J. T., Gong, J., Orouji, S., Esufali, J., Mallick, A. I., Parvizi, P., Shewen, P. E., and Sharif, S. (2011). Oral treatment of chickens with lactobacilli influences elicitation of immune responses. Clin. Vaccine Immunol. CVI 18, 1447-1455.

Carver, D. K., Fetrow, J., Gerig, T., Krueger, T., and Barnes, H. J. (2002). Hatchery and transportation factors associated with early poult mortality in commercial turkey flocks. Poult. Sci. 81, 1818-1825.

Cox, L. M., Yamanishi, S., Sohn, J., Alekseyenko, A. V., Leung, J. M., Cho, I., Kim, S., Li, H., Gao, Z., Mahana, D., et al. (2014). Altering the intestinal microbiota during a critical developmental window has lasting metabolic consequences. Cell 158, 705-721.

Danzeisen, J. L., Calvert, A. J., Noll, S. L., McComb, B., Sherwood, J. S., Logue, C. M., and Johnson, T. J. (2013). Succession of the turkey gastrointestinal bacterial microbiome related to weight gain. PeerJ 1, e237.

Gadde, U. D., Oh, S., Lee, Y., Davis, E., Zimmerman, N., Rehberger, T., and Lillehoj, H. S. (2017). Dietary *Bacillus subtilis*-based direct-fed microbials alleviate LPS-induced intestinal immunological stress and improve intestinal barrier gene expression in commercial broiler chickens. Res. Vet. Sci. 114, 236-243.

Georgopoulou, J., Lordanidis, P., and Bougiouklis, P. (2005). The frequency of respiratory diseases in broiler chickens during 1992-2001. Delt. Tes Ellenikes Kteniatr. Etair. J Hell. Vet Med Soc 56, 219-227.

Haghighi, H. R., Gong, J., Gyles, C. L., Hayes, M. A., Zhou, H., Sanei, B., Chambers, J. R., and Sharif, S. (2006). Probiotics stimulate production of natural antibodies in chickens. Clin. Vaccine Immunol. 13, 975-980.

Havenaar, R., and Spanhaak, S. (1994). Probiotics from an immunological point of view. Curr. Opin. Biotechnol. 5, 320-325.

Inoue, R., and Ushida, K. (2003). Vertical and horizontal transmission of intestinal commensal bacteria in the rat model. FEMS Microbiol. Ecol. 46, 213-219.

Jin, L. Z., Ho, Y. W., Abdullah, N., and Jalaludin, S. (1998). Growth performance, intestinal microbial populations, and serum cholesterol of broilers fed diets containing *Lactobacillus* cultures. Poult. Sci. 77, 1259-1265.

Johnson, T. J., Wannemuehler, Y., Doetkott, C., Johnson, S. J., Rosenberger, S. C., and Nolan, L. K. (2008). Identification of minimal predictors of Avian Pathogenic *Escherichia coli* virulence for use as a rapid diagnostic tool. J. Clin. Microbiol. 46, 3987-3996.

Kerr, A. K., Farrar, A. M., Waddell, L. A., Wilkins, W., Wilhelm, B. J., Bucher, O., Wills, R. W., Bailey, R. H., Varga, C., McEwen, S. A., et al. (2013). A systematic review-meta-analysis and meta-regression on the effect of selected competitive exclusion products on *Salmonella* spp. prevalence and concentration in broiler chickens. Prev. Vet. Med. 111, 112-125.

Konsak, B. M., Stanley, D., Haring, V. R., Geier, M. S., Hughes, R. J., Howarth, G. S., Crowley, T. M., and Moore, R. J. (2013). Identification of differential duodenal gene expression levels and microbiota abundance correlated with differences in energy utilisation in chickens. Anim. Prod. Sci. 53, 1269-1275.

La Ragione, R. M., Casula, G., Cutting, S. M., and Woodward, M. J. (2001). *Bacillus subtilis* spores competitively exclude *Escherichia coli* O78:K80 in poultry. Vet. Microbiol. 79, 133-142.

Martin-Vivaldi, M., Soler, J. J., Peralta-Sanchez, J. M., Arco, L., Martin-Platero, A. M., Martinez-Bueno, M., Ruiz-Rodriguez, M., and Valdivia, E. (2014). Special structures of hoopoe eggshells enhance the adhesion of symbiont-carrying uropygial secretion that increase hatching success. J. Anim. Ecol. 83, 1289-1301.

Nascimento, E. R., and Nascimento, M. G. F. (1994). Eradication of *Mycoplasma* gallisepticum and *M. synoviae* from a chicken flock in Brazil. West. Poult. Dis. Conf.

Oakley, B. B., and Kogut, M. H. (2016). Spatial and temporal changes in the broiler chicken cecal and fecal microbiomes and correlations of bacterial taxa with cytokine gene expression. Front. Vet. Sci. 3, 11.

Pedroso, A. A., Menten, J. F. M., and Lambais, M. R. (2005). The structure of bacterial community in the intestines of newly hatched chicks. J. Appl. Poult. Res. 14, 232-237.

Ranjitkar, S., Lawley, B., Tannock, G., and Engberg, R. M. (2016). Bacterial succession in the broiler gastrointestinal tract. Appl. Environ. Microbiol. 82, 2399-2410.

Rolfe, R. D. (2000). The role of probiotic cultures in the control of gastrointestinal health. J. Nutr. 130, 396S-402S.

Ruiz-Rodriguez, M., Soler, J. J., Martin-Vivaldi, M., Martin-Platero, A. M., Mendez, M., Peralta-Sanchez, J. M., Ananou, S., Valdivia, E., and Martinez-Bueno, M. (2014). Environmental factors shape the community of symbionts in the hoopoe uropygial gland more than genetic factors. Appl. Environ. Microbiol. 80, 6714-6723.

Songer, J. G. (1996). Clostridial enteric diseases of domestic animals. Clin. Microbiol. Rev. 9, 216-234.

Stanley, D., Denman, S. E., Hughes, R. J., Geier, M. S., Crowley, T. M., Chen, H., Haring, V. R., and Moore, R. J. (2012). Intestinal microbiota associated with differential feed conversion efficiency in chickens. Appl. Microbiol. Biotechnol. 96, 1361-1369.

Stanley, D., Geier, M. S., Hughes, R. J., Denman, S. E., and Moore, R. J. (2013). Highly variable microbiota development in the chicken gastrointestinal tract. PLoS ONE 8, e84290.

Stanley, D., Hughes, R. J., and Moore, R. J. (2014). Microbiota of the chicken gastrointestinal tract: influence on health, productivity and disease. Appl. Microbiol. Biotechnol. 98, 4301-4310.

Tagg, J. R., Dajani, A. S., and Wannamaker, L. W. (1976). Bacteriocins of gram-positive bacteria. Bacteriol. Rev. 40, 722-756.

Yin, Y., Lei, F., Zhu, L., Li, S., Wu, Z., Zhang, R., Gao, G. F., Zhu, B., and Wang, X. (2009). Exposure of different bacterial inocula to newborn chicken affects gut microbiota development and ileum gene expression. ISME J. 4, 367-376.

---

We claim:

1. A method of improving bird performance, comprising:
introducing into the gastrointestinal tract of one or more birds on the day-of hatch an effective amount of the direct fed microbial composition comprising at least one *Bacillus* strain and at least one *Lactobacillus* strain;
wherein the at least one *Lactobacillus* strain is chosen from at least one of strains *Lactobacillus plantarum* Lp-115 and *Lactobacillus salivarius* Ls-33; and the at least one *Bacillus* strain is chosen from at least one of strains *Bacillus subtilis* 747 deposited as NRRL B-67257, *Bacillus subtilis* 967, *Bacillus subtilis* 1104 deposited as NRRL B-67258, *Bacillus subtilis* 1145, *Bacillus subtilis* 1541 deposited as NRRL B-67260, *Bacillus subtilis* 1781 deposited as NRRL B-67259, *Bacillus subtilis* 1999 deposited as NRRL B-67318, and *Bacillus subtilis* 2018 deposited as NRRL B-67261;
wherein the ratio of the at least one *Lactobacillus* strain to the at least one *Bacillus* strain in said direct fed microbial composition is at least about 4:1;
wherein the effective amount of said direct fed microbial composition comprises a concentration of the isolated *Bacillus* strain of between about $2.5 \times 10^7$ CFU/bird and about $1.0 \times 10^9$ CFU/bird and a concentration of the isolated *Lactobacillus* strain of between about $2.5 \times 10^7$ CFU/bird and about $1.0 \times 10^9$ CFU/bird;
and wherein the introduction of the direct fed microbial composition provides at least one benefit chosen from:
inhibiting a pathogen chosen from at least one of *Escherichia coli*, *Clostridium perfringens* and Enterobacteriaceae in the one or more birds;
decreasing a mortality rate of the one or more birds;
improving the coefficient of variation of weight of the one or more birds;
reducing the occurrence of necrotic enteritis in the one or more birds;
reducing the occurrence of colibacillosis in the one or more birds; and
modulating immune responses of inflammatory cytokines in gastrointestinal epithelial cells in the one or more birds.

2. The method of claim 1, wherein the at least one *Lactobacillus* strain is *Lactobacillus salivarius* Ls-33, and the administration of the direct fed microbial composition provides the benefit of amelioration of the gastrointestinal inflammatory cytokine response associated with a gram negative bacterial infection in the gastrointestinal tract of the one or more birds.

3. The method of claim 1, wherein the administration of the direct fed microbial composition provides the benefit of eliciting an immunomodulatory effect in gastrointestinal epithelial cells to control inflammatory responses associated with the stress of enteric pathogenic challenges in the one or more birds.

4. The method of claim 1, wherein the introduction step includes:
wetting the direct fed microbial composition;
spraying the wetted composition onto an outer surface of the one or more birds to form droplets; and
inducing a bird to ingest one or more of the droplets from the outer surface of a different bird.

5. The method of claim 4, where in the wetted composition includes a color attractant configured to induce ingestion of the droplets by said birds.

6. The method of claim 1, wherein the ratio of the at least one *Lactobacillus* strain to the at least one *Bacillus* strain in said direct fed microbial composition is at least about 9.1.

* * * * *